US007091220B2

(12) United States Patent
Gerlach et al.

(10) Patent No.: US 7,091,220 B2
(45) Date of Patent: Aug. 15, 2006

(54) SUBSTITUTED INDOLE MANNICH BASES

(75) Inventors: Matthias Gerlach, Brachttal (DE); Corinna Maul, Aachen (DE)

(73) Assignee: Gruenenthal GmbH, Aachen (DE)

( * ) Notice: Subject to any disclaimer, the term of this patent is extended or adjusted under 35 U.S.C. 154(b) by 96 days.

(21) Appl. No.: 10/168,985

(22) PCT Filed: Dec. 20, 2000

(86) PCT No.: PCT/EP00/12974

§ 371 (c)(1), (2), (4) Date: Jun. 26, 2002

(87) PCT Pub. No.: WO01/47885

PCT Pub. Date: Jul. 5, 2001

(65) Prior Publication Data

US 2003/0060497 A1    Mar. 27, 2003

(30) Foreign Application Priority Data

Dec. 27, 1999   (DE) ................................ 199 63 178

(51) Int. Cl.
*A61K 31/445*  (2006.01)
*C07D 209/42*  (2006.01)
*C07D 209/14*  (2006.01)

(52) U.S. Cl. .................. 514/323; 514/235.8; 514/414; 514/415; 544/143; 546/201; 548/468; 548/506

(58) Field of Classification Search ............. 514/235.8, 514/323, 414, 415; 544/143; 546/201; 548/468; 548/506
See application file for complete search history.

(56) References Cited

U.S. PATENT DOCUMENTS

| 3,296,072 | A | * | 1/1967 | Szmuszkovicz et al. | .... 514/415 |
| 3,957,288 | A |   | 5/1976 | Lemahieu et al. | .......... 430/138 |
| 4,341,402 | A |   | 7/1982 | Schmidt et al. | ............. 503/223 |
| 4,785,016 | A |   | 11/1988 | Evans et al. | ................ 514/415 |
| 4,855,448 | A |   | 8/1989 | Walsh | ........................ 548/504 |
| 5,735,301 | A |   | 4/1998 | Rower |

FOREIGN PATENT DOCUMENTS

| CA | 2130294 | | 2/1996 |
| DE | 23 29 430 | | 1/1974 |
| DE | 27 24 809 A1 | | 8/1978 |
| DE | 32 09 305 A1 | | 9/1983 |
| DE | 198 23 326 A1 | | 12/1999 |
| EP | 0 768 301 | | 4/1997 |
| FR | 2 181 559 | | 12/1973 |
| SE | 449 483 B | | 5/1987 |
| WO | 94 14770 | | 7/1994 |
| WO | 94 14771 | | 7/1994 |
| WO | 99 43654 | | 9/1999 |
| WO | WO 01/47882 | * | 7/2001 |
| WO | WO 01-47882 | * | 7/2001 |
| WO | WO 01/51226 A1 | | 7/2001 |

OTHER PUBLICATIONS

Vlasova et al. "New synthesis of substituted gramines" CA 98:143226 (1983).*
Grumbach et al. "Aminoalkylation of electron-rich compounds . . . " CA 125:167739 (1996).*
Couper et al. "Serotonin injections induce metamorphosis . . . " CA 126:29328 (1996).*
March "Advanced organic chemistry . . . " McGraw-Hill, p. 670 (1968).*
Vlasova et al. "New synthesis . . . " Ca 98:143226 (1983).*
Grumbach et al. "Aminoalkylation . . . " CA 125:167739 (1996).*
Maul et al. "Preparation of 3-amino . . . " CA.135:92540 (2001).*
Mocek et al. "Chemical purification and . . . " CA 126:311636 (1997).*
H-J. Grumbach, et al., Synthesis, pp. 883-887, "Aminoalkylation of Electron-Rich Aromatic Compounds Using Preformed Iminium Salts Derived From Aldehydes Other Than Formaldehyde", Jul. 1996.
T. Moriya, et al., Synthesis, pp. 728-730, "A New, Facile Synthesis of 3-(1-Dialkylaminoalkyl)-1H-Indoles", Sep. 1980.
L. C. Hendershot, et al., Journal of Pharmacology and Exp. Ther., vol. 125, pp. 237-240, "Antagonism of the Frequency of Phenylquinone-Induced Writhing in the Mouse by Weak Analgesics and Nonanalgesics", 1959.
O. Jeanneton, et al., The Journal Pharmacology and Experimental Therapeutics, vol. 267, No. 1, pp. 31-37, "Platelet-Activating Factor (PAF) Induces a Contraction of Isolated Smooth Muscle Cells From Guinea Iieum: Intracellular Pathway Involved", 1993.
M. Ch. Frink, et al., Arzneim.-Forsch./Drug. Res, vol. 46 (II), No. 11, pp. 1029-1036, "Influence of Tramadol on Neurotransmitter Systems of the Rat Brain", 1996.
E. G. Gray, et al., J. Anat 76, pp. 79-88, "The Isolation of Nerve Endings From Brain: an Electron-Microsocopic Study of Cell Fragments Derived by Homogenization and Centrifugation", 1962.
M.I. Vlasova et al.: "New synthesis of substituted gramines" Chemical Abstracts, vol. 98, No. 17 Apr. 25, 1983.
Robert W. Huffman et al.: "Reaction of indolenine salts with nucleophiles" J. Am. Chem. Soc., vol. 89, No. 24, pp. 6243-6251 1967.
D.M. Tabidze et al.: "Bisindoles, 15. acid condensation of 2,2'-ethoxycarbonyl derivatives of bis(5-indolyl) oxide and bis(5-indolyl)methane with aromatic aldehydes" Chemical Abstracts, vol. 99, No. 3 Jul. 18, 1983.

* cited by examiner

*Primary Examiner*—Celia Chang
(74) *Attorney, Agent, or Firm*—Oblon, Spivak, McClelland, Maier & Neustadt, P.C.

(57) ABSTRACT

The present invention relates to substituted indole Mannich bases, processes of preparing substituted indole Mannich base, a medicament containing the same, and a pharmaceutical composition containing the same.

98 Claims, 2 Drawing Sheets

SUBSTITUTED INDOLE MANNICH BASES

Figure 1:
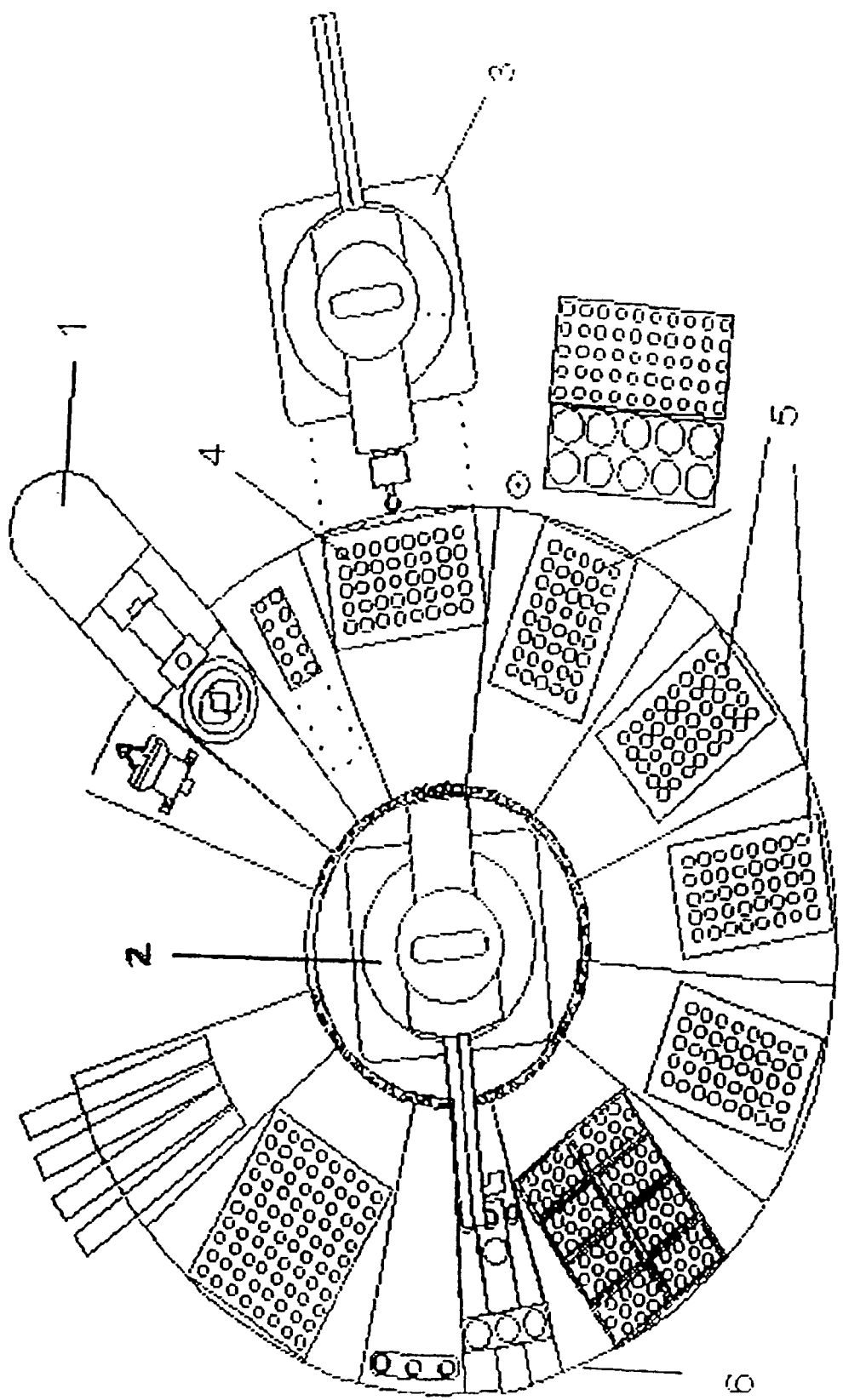

The invention relates to substituted indole Mannich bases, processes for their preparation, medicaments comprising these compounds and the use of these compounds for the preparation of medicaments.

Pain is one of the basic clinical symptoms. There is a worldwide need for effective pain treatment. The urgent need for action for target-orientated treatment of chronic and non-chronic states of pain appropriate for the patient, by which is to be understood successful and satisfactory pain treatment for the patient, is documented in the large number of scientific works which have been published in the field of applied analgesia and basic research in nociception in recent years.

Conventional opioids, such as e.g. morphine, are effective in the treatment of severe to very severe pain. However, they have as undesirable concomitant symptoms, inter alia, respiratory depression, vomiting, sedation, constipation and development of tolerance.

Tramadol hydrochloride—(1RS,2RS)-2-[(dimethylamino)methyl]-1-(3-methoxyphenyl)-cyclohexanol—occupies a special position among analgesics having an action on the central nervous system, since this active compound brings about potent inhibition of pain without the side effects known of opioids (J. Pharmacol. Exptl. Ther. 267, 33 (1993)). Research is being conducted worldwide into further pain-inhibiting agents.

The object of the present invention was therefore to provide new compounds which are suitable in particular as active compounds in medicaments.

These active compounds should be suitable in particular for pain treatment and for treatment of inflammatory and allergic reactions, drug and/or alcohol abuse, diarrhoea, gastritis, ulcers, cardiovascular diseases, urinary incontinence, depression, states of shock, migraines, narcolepsy, excess weight, asthma, glaucoma, hyperkinetic syndrome, lack of drive, bulimia, anorexia and/or catalepsy, for anxiolysis, for increasing vigilance and/or for increasing libido.

This object is achieved according to the invention by providing substituted indole Mannich bases of the following general formula I which have a pronounced analgesic action, in particular also on chronic pain, and which moreover are suitable for treatment of/combating inflammatory and allergic reactions, drug and/or alcohol abuse, diarrhoea, gastritis, ulcers, cardiovascular diseases, urinary incontinence, depression, states of shock, migraines, narcolepsy, excess weight, asthma, glaucoma, hyperkinetic syndrome, lack of drive, bulimia, anorexia and/or catalepsy, for anxiolysis, for increasing vigilance and/or for increasing libido.

The present invention therefore relates to substituted indole Mannich bases of the general formula I

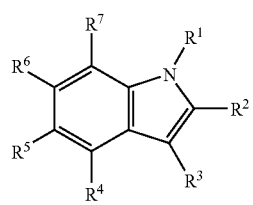

I wherein
$R^1$=H, a $C_{1-10}$-alkyl radical or an aryl or heteroaryl radical bonded via a $C_{1-6}$-alkylene group, preferably H, a $C_{1-6}$-alkyl radical or an aryl radical bonded via a $C_{1-2}$-alkylene group, particularly preferably H or a $C_{1-2}$-alkyl radical, $R^2$=H, F, Cl, Br, $CF_3$, CN, $NO_2$, $NHR^8$, $SR^9$, $OR^{10}$, $SO_2NH_2$, $SO_2NHR^{21}$, $CO(OR^{11})$, $CH_2CO(OR^{12})$, $COR^{19}$, a $C_{1-10}$-alkyl, an aryl or a heteroaryl radical or an aryl or heteroaryl radical bonded via a $C_{1-6}$-alkylene group, preferably=H, Cl, F, $NO_2$, $OR^{10}$, $CO(OR^{11})$, a $C_{1-6}$-alkyl radical or an aryl radical bonded via a $C_{1-2}$-alkylene group, particularly preferably H, a $C_{1-2}$-alkyl radical or an unsubstituted phenyl radical, $R^3$=$CH(R^{13})N(R^{14})(R^{15})$, $R^4$, $R^5$, $R^6$, $R^7$ are identical or different and=H, F, Cl, Br, $CF_3$, CN, $NO_2$, $NHR^8$, $SR^9$, $OR^{10}$, $SO_2NH_2$, $SO_2NHR^{21}$, $CO(OR^{11})$, $CH_2CO(OR^{12})$, $COR^{19}$, a $C_{1-10}$-alkyl, an aryl or a heteroaryl radical or an aryl or heteroaryl radical bonded via a $C_{1-6}$-alkylene group, preferably=H, Cl, F, $NO_2$, $OR^{10}$, $CO(OR^{11})$, an aryl radical, a $C_{1-6}$-alkyl radical or an aryl radical bonded via a $C_{1-2}$-alkylene group, particularly preferably H, $NO_2$, a $C_{1-2}$-alkyl radical or an unsubstituted phenyl radical, $R^8$=H, $COR^{16}$ or a $C_{1-10}$-alkyl or an aryl radical, preferably a $C_{1-6}$-alkyl radical, $R^9$=H or a $C_{1-10}$-alkyl or an aryl radical, preferably a $C_{1-6}$-alkyl or a phenyl radical, $R^{10}$=H, $COR^{17}$, a $C_{1-10}$-alkyl or an aryl radical or an aryl or heteroaryl radical bonded via a $C_{1-6}$-alkylene group, preferably=H, a $C_{1-6}$-alkyl radical or an aryl radical bonded via a $C_{1-12}$-alkylene group, $R^{11}$=H or a $C_{1-10}$-alkyl or an aryl radical, preferably=H or a $C_{1-6}$-alkyl radical, $R^{12}$=H, a $C_{1-10}$-alkyl radical or an aryl radical, preferably a $C_{1-6}$-alkyl radical, $R^{13}$=an unsubstituted phenyl radical or a phenyl radical which is at least monosubstituted by $C_{1-4}$-alkyl, $C_{1-3}$-alkoxy, halogen, $CF_3$, CN, O-phenyl or OH, preferably an unsubstituted phenyl radical or a phenyl radical which is at least monosubstituted by methyl, tert-butyl, methoxy, F, Cl, Br or $CF_3$, particularly preferably an unsubstituted phenyl radical or a 2-methoxy-phenyl, 3-methoxy-phenyl, 4-methoxy-phenyl, 2-methyl-phenyl, 3-methyl-phenyl, 4-methyl-phenyl, 2-tert-butyl-phenyl, 3-tert-butyl-phenyl, 4-tert-butyl-phenyl, 2-fluoro-phenyl, 3-fluoro-phenyl, 4-fluoro-phenyl, 2-chloro-phenyl, 3-chloro-phenyl, 4-chloro-phenyl, 2-bromo-phenyl, 3-bromo-phenyl, 4-bromo-phenyl, 5-bromo-2-fluoro-phenyl, 2-chloro-4-fluoro-phenyl, 2-chloro-5-fluoro-phenyl, 2-chloro-6-fluoro-phenyl, 4-bromo-2-fluoro-phenyl, 3-bromo-4-fluoro-phenyl, 3-bromo-2-fluoro-phenyl, 2,3-dichloro-phenyl, 2,4-dichloro-phenyl, 2,5-dichlorophenyl, 3,4-dichloro-phenyl, 2,3-dimethyl-phenyl, 2,4-dimethyl-phenyl, 2,5-dimethylphenyl, 2,3-dimethoxy-phenyl, 2,4-dimethoxy-phenyl, 2,5-dimethoxy-phenyl, 3,4-dimethoxy-phenyl, 3,4,5-trimethoxy-phenyl, 2-trifluoromethyl-phenyl, 3-trifluoromethyl-phenyl or 4-trifluoromethyl-phenyl radical, very particularly preferably an unsubstituted phenyl radical, $R^{14}$, $R^{15}$ are identical or different and denote a branched or unbranched, saturated or unsaturated, unsubstituted or at least monosubstituted $C_{1-6}$-alkyl radical or an unsubstituted or at least monosubstituted phenyl, benzyl or phenethyl radical, preferably a saturated, unsubstituted or at least monosubstituted $C_{1-6}$-alkyl radical, particularly preferably a $CH_3$ radical, or $R^{14}$ and $R^{15}$ together denote $(CH_2)_n$, where n=an integer from 3 to 6, or $(CH_2)_2O(CH_2)_2$, preferably $(CH_2)_n$, where n=4 or 5, $R^{16}$=a $C_{1-10}$-alkyl, an aryl or a heteroaryl radical, preferably a $C_{1-6}$-alkyl radical, $R^{17}$=a $C_{1-10}$-alkyl radical, preferably a $C_{1-6}$-alkyl radical, $R^{18}$=a $C_{1-10}$-alkyl, an aryl, a heteroaryl or a naphthyl radical, preferably a $C_{1-6}$-alkyl radical, $R^{19}$=H, $NHNH_2$, $NHR^{20}$, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{20}$=H, a $C_{1-10}$-alkyl, an aryl or a heteroaryl radical or an aryl or heteroaryl radical bonded via a $C_{1-6}$-alkylene group, preferably a $C_{1-6}$-alkyl radical or an aryl radical bonded via a $C_{1-2}$-alkylene group, $R^{21}$=H, $COR^{17}$, a $C_{1-6}$-alkyl or an aryl radical or an aryl or heteroaryl radical bonded via a $C_{1-6}$-alkylene group, preferably=H, a $C_{1-6}$-alkyl radical or an aryl radical bonded via a $C_{1-2}$-alkylene group and/or their racemates, enantiomers, diastereomers and/or corresponding bases and/or corresponding salts of physiologically tolerated acids, excluding the racemates of the compounds in which the radical $R^3$=CH($R^{13}$)N($R^{14}$)($R^{15}$) and in each case the radicals $R^4$ to $R^7$ and $R^2$=H, the radical $R^{13}$=phenyl, the radicals $R^{14}$ and $R^{15}$ together=$(CH_2)_5$ and the radical $R^1$=H, $CH_3$ or benzyl or the radicals $R^4$ to $R^7$ and $R^2$=H, the radical $R^{13}$=phenyl, the radicals $R^{14}$, $R^{15}$ each=$CH_3$ and the radical $R^1$=H, $CH_3$ or benzyl or the radicals $R^4$ to $R^7$ and $R^1$=H, the radical $R^{13}$=2-chlorophenyl, the radicals $R^{14}$ and $R^{15}$ each=$CH_3$ or the radicals $R^{14}$ and $R^{15}$ together=$(CH_2)_2O(CH_2)_2$, the radical $R^2$=$COOR^{11}$ and the radical $R^{11}$=$C_2H_5$ and the corresponding hydrochlorides or the radicals $R^4$ to $R^7$ and $R^1$=H, the radical $R^{13}$=phenyl, the radicals $R^{14}$ and $R^{15}$ together=$(CH_2)_5$, the radical $R^2$=$COOR^{11}$ and the radical $R^{11}$=$CH_3$ as the hydrochloride or the radicals $R^4$ to $R^7$ and $R^2$=H, the radical $R^{13}$=phenyl, the radicals $R^{14}$ and $R^{15}$ together=$(CH_2)_4$ and the radical $R^1$=H, $CH_3$, $CH_2$—CH=$CH_2$ or 4-chlorobenzyl and for $R_1$=$CH_3$ also the corresponding hydrochloride of the compound or the radicals $R^4$ to $R^7$, $R^1$ and $R^2$=H, the radical $R^{13}$=phenyl, the radical $R^{14}$=phenyl and the radical $R^{15}$=4-ethoxyphenyl or the radicals $R^4$ to $R^7$=H, the radical $R^{13}$=2,4,6-trimethoxyphenyl, the radicals $R^{14}$ and $R^{15}$ together=$(CH_2)_2O(CH_2)_2$, the radical $R^1$=$CH_3$ and the radical $R^2$=phenyl or the radicals $R^4$ to $R^7$ and $R^1$=H, the radical $R^{13}$=phenyl, 2-hydroxyphenyl or 2-hydroxy-5-methylphenyl, the radicals $R^{14}$ and $R^{15}$ together=$(CH_2)_5$ and the radical $R^2$=$CH_3$ and for $R^{13}$=phenyl also the corresponding hydrogen sulfate or the radicals $R^4$ to $R^7$ and $R^1$=H, the radical $R^{13}$=phenyl, the radicals $R^{14}$ and $R^{15}$ together=$(CH_2)_2O(CH_2)_2$ and the radical $R^2$=$CH_3$ and the corresponding hydrogen sulfate of the compound or the radicals $R^4$ to $R^7$ and $R^1$=H, the radical $R^{13}$=phenyl, the radicals $R^{14}$ and $R^{15}$ together=$(CH_2)_5$, the radical $R^2$=$COOR^{11}$ and the radical $R^{11}$=$CH_3$ as the hydrochloride or the radicals $R^1$, $R^4$, $R^6$, $R^7$=H, the radical $R^2$=$COOR^{11}$, the radical $R^{11}$=$C_2H_5$, the radicals $R^{14}$ and $R^{15}$ each=$CH_3$, the radical $R^{13}$=2-chlorophenyl and the radical $R^5$=3-[(2-chlorophenyl)-dimethylaminomethyl]-5-methylene-1H-indole-2-carboxylic acid ethyl ester or 3-[(2-chlorophenyl)-dimethylaminomethyl]-5-hydroxate-1H-indole-2-carboxylic acid ethyl ester.

Alkyl radicals are preferably understood as hydrocarbon radicals which are at least monosubstituted by halogen, OH, CN or $CF_3$, particularly preferably by F, Cl, Br or OH. If these contain more than one substituent, these substituents can be identical or different. The alkyl radicals can be branched, unbranched or cyclic. The alkyl radicals methyl, ethyl, propyl, 1-methylethyl, butyl, 1-methylpropyl, 2-methylpropyl, 1,1-dimethylpropyl, 1,2-dimethylpropyl, 2,2-dimethylpropyl, hexyl, 1-methylpentyl, heptyl, nonyl or decanyl are particularly preferred.

An aryl radical is preferably understood as phenyl or naphthyl radicals which are at least monosubstituted by an OH, a halogen, preferably F, Br or Cl, a $CF_3$, a CN, a $C_{1-6}$-alkyl, a $C_{1-6}$-alkoxy or a phenyl radical. The unsubstituted or substituted phenyl radicals can also be fused with further rings. The aryl radicals 2-, 3- and 4-bromophenyl, 4-bromo-2-fluorophenyl, 5-bromo-2-fluorophenyl, 3-bromo-4-fluorophenyl, 4-tert-butylphenyl, 2-chloro-4-fluorophenyl, 2-chloro-6-fluorophenyl, 4-cyanophenyl, 2,3-dichlorophenyl, 2,4-dichlorophenyl, 2,6-dichlorophenyl, 3,4-dichlorophenyl, 2,3-dimethoxyphenyl, 3,4-dimethoxyphenyl, 2,4-dimethylphenyl, 2,5-dimethylphenyl, 2-, 3- and 4-fluorophenyl, 2-methoxyphenyl, 2-, 3- and 4-methylphenyl, 3-phenoxyphenyl, 2- and 4-trifluoromethylphenyl or 3,4,5-trimethoxyphenyl are particularly preferred.

A heteroaryl radical is understood as aromatic compounds which have at least one heteroatom, preferably nitrogen and/or oxygen and/or sulfur, particularly preferably nitrogen and/or oxygen, and which can preferably be substituted by a halogen, CN, $CF_3$ or OH radical. The heteroaryl is particularly preferably a substituted or unsubstituted thiophene, pyrrolyl or furfuryl radical.

The following substituted indole Mannich bases are particularly preferred:

3-(dimethylaminophenylmethyl)-1H-indole-2-carboxylic acid ethyl ester 3-(dimethylaminophenylmethyl)-1H-indole-2-carboxylic acid

[(5-fluoro-1H-indol-3-yl)-phenylmethyl]-dimethylamine

[(1-ethyl-2-phenyl-1H-indol-3-yl)-phenylmethyl]-dimethylamine

[(5-methoxy-1H-indol-3-yl)-phenylmethyl]-dimethylamine 3-(dimethylaminophenylmethyl)-5-hydroxy-1H-indole-2-carboxylic acid dimethyl-[(2-methyl-1H-indol-3-yl)-phenylmethyl]-amine 3-(dimethylaminophenylmethyl)-1H-indol-4-ol dimethyl-[(4-methyl-1H-indol-3-yl)-phenylmethyl]-amine

[(5-chloro-1H-indol-3-yl)-phenylmethyl]-dimethylamine

[(5-benzyloxy-1H-indol-3-yl)-phenylmethyl]-dimethylamine acetic acid 3-(dimethylaminophenylmethyl)-1H-indol-4-yl ester {[2-(4-chlorophenyl)-1H-indol-3-yl]-phenylmethyl}-dimethylamine 5-benzyloxy-3-(dimethylaminophenylmethyl)-1H-indole-2-carboxylic acid dimethyl-[(2-methyl-5-nitro-1H-indol-3-yl)-phenylmethyl]-amine dimethyl-[(2-methyl-6-nitro-1H-indol-3-yl)-phenylmethyl]-amine

[(6-fluoro-2-methyl-1H-indol-3-yl)-phenylmethyl]-dimethylamine

{[2-(4-fluorophenyl)-1H-indol-3-yl]-phenylmethyl}-dimethylamine

{[2-(3-chloro-4-fluorophenyl)-1H-indol-3-yl]-phenylmethyl}-dimethylamine
[(7-ethyl-1H-indol-3-yl)-phenylmethyl]-dimethylamine
3-(dimethylaminophenylmethyl)-1H-indole-6-carboxylic acid
dimethyl-[(1-methyl-1H-indol-3-yl)-phenylmethyl]-amine
1-methyl-3-(morpholin-4-yl-phenylmethyl)-1H-indole
3-[(2-methoxyphenyl)-pyrrolidin-1-yl-methyl]-1-methyl-1H-indole
1-ethyl-2-phenyl-3-(pyrrolidin-1-yl-o-tolylmethyl)-1H-indole
3-[(2-chlorophenyl)-piperidin-1-yl-methyl]-1-ethyl-2-phenyl-1H-indole
1-ethyl-2-phenyl-3-(phenylpyrrolidin-1-yl-methyl)-1H-indole
1-ethyl-3-[(2-methoxyphenyl)-pyrrolidin-1-yl-methyl]-2-phenyl-1H-indole
2-phenyl-3-(pyrrolidin-1-yl-o-tolylmethyl)-1H-indole
2-phenyl-3-(piperidin-1-yl-o-tolylmethyl)-1H-indole
3-[(2-chlorophenyl)-piperidin-1-yl-methyl]-2-phenyl-1H-indole
dimethyl-[(2-phenyl-1H-indol-3-yl)-o-tolyl-methyl]-amine
2-phenyl-3-(phenylpyrrolidin-1-yl-methyl)-1H-indole
3-[(2-methoxy-phenyl)-pyrrolidin-1-yl-methyl]-2-phenyl-1H-indole
4-methyl-3-(piperidin-1-yl-o-tolyl-methyl)-1H-indole
3-[(2-methoxyphenyl)-pyrrolidin-1-yl-methyl]-4-methyl-1H-indole
5-benzyloxy-3-(phenyl-piperidin-1-yl-methyl)-1H-indole
[(5-benzyloxy-1H-indol-3-yl)-o-tolylmethyl]-dimethylamine
7-ethyl-3-[(2-methoxyphenyl)-morpholin-4-yl-methyl]-1H-indole
3-[(2-methoxyphenyl)-piperidin-1-yl-methyl]-2-phenyl-1H-indole
5-chloro-3-[(2-methoxyphenyl)-piperidin-1-yl-methyl]-1H-indole
5-chloro-3-[(2-methoxyphenyl)-pyrrolidin-1-yl-methyl]-1H-indole
5-benzyloxy-3-[(2 methoxyphenyl)-pyrrolidin-1-yl-methyl]-1H-indole
[(2-methoxyphenyl)-(2-methyl-1H-indol-3-yl)-methyl]-dimethylamine
{[1-(4-methoxybenzyl)-1H-indol-3-yl]-phenyl-methyl}-dimethylamine
3-(phenylpiperidin-1-yl-methyl)-1H-indole
1-methyl-3-(phenylpiperidin-1-yl-methyl)-1H-indole
3-(phenylpyrrolidin-1-yl-methyl)-1H-indole
[(1H-indol-3-yl)-phenylmethyl]-dimethylamine
5-benzyloxy-3-(phenyl-pyrrolidin-1-yl-methyl)-1H-indole
[(5-bromo-2-fluoro-phenyl)-(4-nitro-1H-indol-3-yl)-methyl]-dimethyl-amine
[(5-bromo-2-fluoro-phenyl)-(1-methyl-1H-indol-3-yl)-methyl]-dimethyl-amine
[(2-chloro-6-fluoro-phenyl)-(2-phenyl-1H-indol-3-yl)-methyl]-dimethylamine
[(2-chloro-6-fluoro-phenyl)-(1-ethyl-2-phenyl-1H-indol-3-yl)-methyl]-dimethylamine
[(2-chloro-6-fluoro-phenyl)-(4-nitro-1H-indol-3-yl)-methyl]-dimethyl-amine
[(2-chloro-6-fluoro-phenyl)-(1-methyl-1H-indol-3-yl)-methyl]-dimethyl-amine
[(2-bromo-phenyl)-(4-nitro-1H-indol-3-yl)-methyl]-dimethyl-amine
[(2-bromo-phenyl)-(1-methyl-1H-indol-3-yl)-methyl]-dimethyl-amine
[(3-bromo-phenyl)-(7-ethyl-1H-indol-3-yl)-methyl]-dimethyl-amine
[(3-bromo-phenyl)-(1-methyl-1H-indol-3-yl)-methyl]-dimethyl-amine
[(4-tert-butyl-phenyl)-(2-methyl-1H-indol-3-yl)-methyl]-dimethyl-amine
[(4-tert-butyl-phenyl)-(1-ethyl-2-phenyl-1H-indol-3-yl)-methyl]-dimethyl-amine
[(4-tert-butyl-phenyl)-(1-methyl-1H-indol-3-yl)-methyl]-dimethyl-amine
[(2-chloro-4-fluoro-phenyl)-(4-nitro-1H-indol-3-yl)-methyl]-dimethyl-amine
[(2-chloro-4-fluoro-phenyl)-(4-methyl-1H-indol-3-yl)-methyl]-dimethyl-amine
[(2-chloro-6-fluoro-phenyl)-(2-phenyl-1H-indol-3-yl)-methyl]-dimethyl-amine
{(2-chloro-6-fluoro-phenyl)-[2-(4-chloro-phenyl)-1H-indol-3-yl]-methyl}-dimethyl-amine
[(2-chloro-6-fluoro-phenyl)-(1-methyl-1H-indol-3-yl)-methyl]-dimethyl-amine
[(3-chloro-phenyl)-(1-methyl-1H-indol-3-yl)-methyl]-dimethyl-amine
[(2,3-dichloro-phenyl)-(1-methyl-1H-indol-3-yl)-methyl]-dimethyl-amine
[(2,4-dichloro-phenyl)-(1-methyl-1H-indol-3-yl)-methyl]-dimethyl-amine
[(4-tert-butyl-phenyl)-(1-ethyl-2-phenyl-1H-indol-3-yl)-methyl]-dimethyl-amine
[(2-chloro-4-fluoro-phenyl)-(2-methyl-1H-indol-3-yl)-methyl]-dimethyl-amine
[(2-chloro-6-fluoro-phenyl)-(2-methyl-1H-indol-3-yl)-methyl]-dimethyl-amine
[(2,3-dimethoxy-phenyl)-(4-nitro-1H-indol-3-yl)-methyl]-dimethylamine
3-[(2,3-dimethoxy-phenyl)-dimethylamino-methyl]-4,7-dihydro-1H-indole-6-carboxylic acid
3-[(2,3-dimethoxy-phenyl)-dimethylamino-methyl]-5-hydroxy-1H-indole-2-carboxylic acid
[(3,4-dimethoxy-phenyl)-2-methyl-1H-indol-3-yl)-methyl]-dimethyl-amine
[[2-(4-chloro-phenyl)-1H-indol-3-yl]-(3,4-dimethoxy-phenyl)-methyl]-dimethyl-amine
[(3,4-dimethoxy-phenyl)-(1-ethyl-2-phenyl-1H-indol-3-yl)-methyl]-dimethyl-amine
[(3,4-dimethoxy-phenyl)-(7-ethyl-1H-indol-3-yl)-methyl]-dimethyl-amine
[(3,4-dimethoxy-phenyl)-(1-methyl-1H-indol-3-yl)-methyl]-dimethyl-amine
[(3,4-diemthoxy-phenyl)-[2-(4-fluoro-phenyl)-1H-indol-3-yl]-methyl)-dimethylamine
[[2-(3-chloro-4-fluoro-phenyl)-1H-indol-3-yl]-(3,4-dimethoxy-phenyl)-methyl]-dimethyl-amine
[(5-chloro-1H-indol-3-yl)-(2-fluoro-phenyl)-methyl]-dimethyl-amine
[(4-fluoro-phenyl)-(4-methyl-1H-indol-3-yl)-methyl]-dimethyl-amine
[(7-ethyl-1H-indol-3-yl)-(2-methoxy-phenyl)-methyl]-dimethyl-amine
dimethyl-[(2-methyl-1H-indol-3-yl)-o-tolyl-methyl]-amine
[(7-ethyl-1H-indol-3-yl)-o-tolyl-methyl]-dimethyl-amine
dimethyl-[(1-methyl-1H-indol-3-yl)-o-tolyl-methyl]-amine
[(5-chloro-1H-indol-3-yl)-o-tolyl-methyl]-dimethyl-amine
[(5-chloro-1H-indol-3-yl)-m-tolyl-methyl]-dimethyl-amine
dimethyl-[(2-methyl-1H-indol-3-yl)-p-tolyl-methyl]-amine
[(5-chloro-1H-indol-3-yl)-p-tolyl-methyl]-dimethyl-amine
dimethyl-[(2-methyl-1H-indol-3-yl)-(3-phenoxy-phenyl)-methyl]-amine

[(1-ethyl-2-phenyl-1H-indol-3-yl)-(3-phenoxy-phenyl)-methyl]-dimethyl-amine

[(7-ethyl-1H-indol-3-yl)-(3-phenoxy-phenyl)-methyl]-dimethyl-amine dimethyl-[(1-methyl-1H-indol-3-yl)-(3-phenoxy-phenyl)-methyl]-amine

[[2-(4-fluoro-phenyl)-1H-indol-3-yl]-(3-phenoxy-phenyl)-methyl]-dimethyl-amine

[[2-(3-chloro-4-fluoro-phenyl)-1H-indol-3-yl]-(3-phenoxy-phenyl)-methyl]-dimethyl-amine dimethyl-[(4-methyl-1H-indol-3-yl)-(3-phenoxy-phenyl)-methyl]-amine

[(5-chloro-1H-indol-3-yl)-(2-trifluoromethyl-phenyl)-methyl]-dimethyl-amine dimethyl-[(2-methyl-1H-indol-3-yl)-(4-trifluoromethyl-phenyl)-methyl]-amine.

The invention also provides processes for the preparation of substituted indole Mannich bases of the general formula I, which are characterized in that aromatic aldehyde compounds of the general formula II

II wherein $R^{13}$ has the meaning according to the general formula I, are reacted in solution, preferably in an organic solvent, particularly preferably in toluene, in the presence of a base, preferably potassium carbonate or boric acid anhydride, at a temperature of preferably −10 to 110° C., with secondary amines of the general formula III

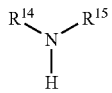

III in which $R^{14}$ and $R^{15}$ have the meaning according to the general formula I, to give aminal compounds of the general formula IV

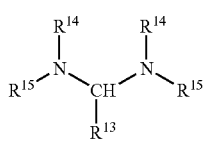

IV and these aminal compounds of the general formula IV are reacted, without further purification, with an acid chloride, preferably with acetyl chloride, in an absolute solvent, preferably in diethyl ether, to give iminium salts of the general formula V

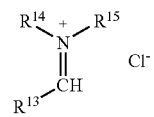

V and these iminium salts of the general formula V are reacted, without further purification and in solution, preferably in acetonitrile and/or toluene, with indole and/or substituted indole compounds of the general formula VI

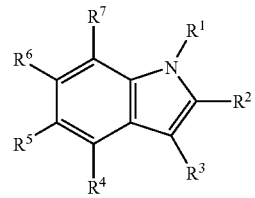

VI in which the radical $R^3$=H and the radicals $R^1$, $R^2$, $R^4$ to $R^{12}$ and $R^{16}$ to $R^{21}$ have the meaning according to the general formula I, and the indole Mannich bases of the general formula I obtained in this way are purified by washing and/or extraction, preferably by washing with acetone, and are isolated by conventional methods.

The invention also provides alternative processes for the preparation of substituted indole Mannich bases of the general formula I in which the radical $R^1$≠H and the radicals $R^2$ to $R^{21}$ have the meaning according to the general formula I, which are characterized in that aromatic aldehyde compounds of the general formula II

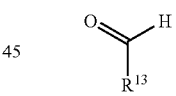

II wherein $R^{13}$ has the meaning according to the general formula I, are reacted in solution, preferably in an organic solvent, particularly preferably in toluene, in the presence of a base, preferably potassium carbonate or boric acid anhydride, at a temperature of preferably −10 to 110° C., with secondary amines of the general formula III

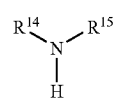

III in which the radicals $R^{14}$ and $R^{15}$ have the meaning according to the general formula I, to give aminal compounds of the general formula IV

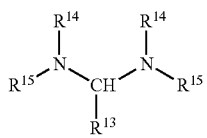

and these aminal compounds of the general formula IV are reacted, without further purification, with an acid chloride, preferably with acetyl chloride, in an absolute solvent, preferably in diethyl ether, to give iminium salts of the general formula V

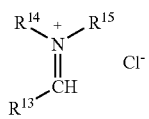

and these iminium salts of the general formula V are reacted, without further purification and in solution, preferably in acetonitrile and/or toluene, with indole and/or substituted indole compounds of the general formula VI

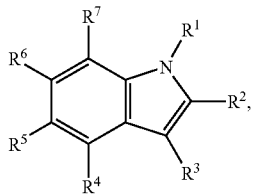

wherein the radicals $R^1$ and $R^3$=H and the radicals $R^2$, $R^4$ to $R^{12}$ and $R^{16}$ to $R^{21}$ have the meaning according to the general formula I, and the compounds of the general formula VI obtained in this way, in which $R^1$=H and the radicals $R^2$ to $R^{21}$ have the meaning according to the general formula I, are reacted in solution, preferably in dimethylsulfoxide, with compounds of the general formula $XR^{22}$, in which the radical $R^{22}$ denotes a $C_{1-10}$-alkyl radical or an aryl or heteroaryl radical bonded via a $C_{1-6}$-alkylene group, preferably a $C_{1-6}$-alkyl radical or an aryl radical bonded via a $C_{1-2}$-alkylene group, and X=Cl, Br or I, preferably Cl, at a temperature of preferably 10 to 150° C. in the presence of a base, preferably triethylamine or potassium tert-butylate, and the compounds of the general formula I obtained in this way, in which $R^1$ represents a $C_{1-10}$-alkyl radical or an aryl or heteroaryl radical bonded via a $C_{1-6}$-alkylene group and the other radicals $R^2$ to $R^{21}$ have the meaning according to the general formula I, are purified by filtration, preferably by filtration over a scavenger resin, particularly preferably by filtration over polymer-bonded tris(2-aminoethyl)-amine (Novabiochem, Bad Soden) and/or 3-(3-mercaptophenyl) propane-amidomethylpolystyrene (Argonaut, Muttenz, Switzerland), and are isolated by conventional methods.

The synthesis of the substituted indole Mannich bases according to the invention is preferably carried out on an automatic unit from Zymark according to FIG. 1 and FIG. 2 as described below.

The substituted indole Mannich bases of the general formula I according to the invention can be converted into their salts in a manner known per se to the expert with physiologically tolerated acids, preferably with hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, particularly preferably in diethyl ether, diisopropyl ether, acetic acid alkyl esters, acetone and/or 2-butanone. The salt formation is very particularly preferably carried out with trimethylchlorosilane in methyl ethyl ketone.

The substituted indole Mannich bases of the general formula I according to the invention are toxicologically acceptable and are therefore suitable pharmaceutical active compounds.

The invention therefore also provides medicaments which comprise, as the active compound, at least one substituted indole Mannich base of the general formula I and optionally further active compounds and/or auxiliary substances.

The medicament can preferably also comprise as the active compound a mixture of enantiomers of at least one substituted indole Mannich base of the general formula I, the mixture preferably not comprising equimolar amounts of the enantiomers. The relative proportion of one of the enantiomers is particularly preferably 5 to 45 mol %, very particularly preferably 10 to 40 mol %, based on the mixture of the enantiomers.

The medicaments are preferably employed for treatment of/combating pain, in particular chronic pain, and/or inflammatory reactions and/or allergic reactions and/or drug abuse and/or alcohol abuse and/or diarrhoea and/or gastritis and/or ulcers and/or cardiovascular diseases and/or urinary incontinence and/or depression and/or states of shock and/or migraines and/or narcolepsy and/or excess weight and/or asthma and/or glaucoma and/or hyperkinetic syndrome and/or lack of drive and/or bulimia and/or anorexia and/or catalepsy and/or for anxiolysis and/or for increasing vigilance and/or for increasing libido.

The present invention also provides the use of at least one substituted indole Mannich base of the general formula I according to the invention for the preparation of a medicament for treatment of/combating pain, in particular chronic pain, and/or inflammatory reactions and/or allergic reactions and/or drug abuse and/or alcohol abuse and/or diarrhoea and/or gastritis and/or ulcers and/or cardiovascular diseases and/or urinary incontinence and/or depression and/or states of shock and/or migraines and/or narcolepsy and/or excess weight and/or asthma and/or glaucoma and/or hyperkinetic syndrome and/or lack of drive and/or bulimia and/or anorexia and/or catalepsy and/or for anxiolysis and/or for increasing vigilance and/or for increasing libido.

In addition to at least one substituted indole Mannich base of the general formula I, carrier materials, fillers, solvents, diluents, dyestuffs and/or binders are employed for formulating appropriate pharmaceutical formulations. The choice of auxiliary substances depends on whether the medicament is to be administered orally, intravenously, intraperitoneally, intradermally, intramuscularly, intranasally, buccally or locally, for example on infections of the skin, the mucous membranes and the eyes. The formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration.

The indole Mannich bases of the general formula I according to the invention in a depot in dissolved form or in a patch, optionally with the addition of agents which promote penetration through the skin, are suitable formulations for percutaneous administration. The compounds of the general formula I according to the invention can be released from oral or percutaneous formulation forms in a delayed manner.

Pharmacological Studies:

1.) In Vitro Tests

Wide-ranging testing of the indole Mannich bases according to the invention for their activity was carried out by the conventional high throughput screening methods, such as are described in John P. Devlin, High Throughput Screening, 1997, Marcel Dekker Inc. They are introduced here as a reference and are therefore part of the disclosure.

The action of the indole Mannich bases according to the invention is determined in particular by the affinity for the N-methyl-D-aspartate (NMDA) receptor family, for (α-adrenergic receptors and opioid receptors.

The investigations of the inhibition of serotonin re-uptake (5-HT uptake inhibition) were carried out by the methods such as are described in M. Ch. Frink, H. -H. -Hennies, W. Englberger, M. Haurand and B. Wilffert, Arzneim.-Forsch./Drug. Res. 46 (III), 11, 1996, pages 1029–1036. They are introduced herewith as reference and thus form part of the disclosure.

To carry out these investigations, synaptosomes were freshly isolated from rat brain areas. In each case the so-called "P2" fraction was used, which was prepared according to the instructions in E. G. Gray and V. P. Whittaker, J. Anat. 76, pages 79–88, 1962. This literature is introduced herewith as reference and thus forms part of the disclosure. For determination of the 5-HT uptake, these vesicular particles were isolated from the pons and medulla oblongata region of the male rat brain.

The following characteristic data were determined for the 5-HT transporter:

5-HT uptake: $K_m = 0.084 \pm 0.011$ μM $V_{max}$: 38.13±4.52 pmol/min/mg protein.

The results of the investigations are in each case stated as means from 2 parallel experiments.

2.) Analgesia Test in the Writhing Test in Mice

The in-depth investigation of the compounds according to the invention for their analgesic activity was carried out in the phenylquinone-induced writhing in mice (modified by I. C. Hendershot, J. Forsaith, J. Pharmacol. Exp. Ther. 125, 237–240 (1959)). Male NMRI mice weighing 25–30 g were used for this. Groups of 10 animals per substance dose received 0.3 ml/mouse of a 0.02% aqueous solution of phenylquinone (phenylbenzoquinone, Sigma, Deisenhofen; preparation of the solution with the addition of 5% ethanol and storage in a water bath at 45° C.) administered intraperitoneally 10 minutes after intravenous administration of the test substances. The animals were placed individually in observation cages. The number of pain-induced stretching movements (so-called writhing reactions=straightening of the body with stretching of the hind extremities) were counted by means of a push-button counter for 5–20 minutes after the administration of phenylquinone. Animals which received only physiological saline solution were also run as a control.

The substances were tested in the standard dose of 10 mg/kg. The inhibition of the writhing reactions by a substance was calculated according to the following equation:

$$\% \text{ inhibition} = 100 - \left[ \frac{\text{writhing reaction of treated animals}}{\text{writhing reaction of control}} \times 100 \right]$$

The following examples serve to illustrate the invention, but do not limit the general inventive idea.

EXAMPLES

General Synthesis Instructions for the Preparation of Aminal Compounds of the General Formula IV:

General Synthesis Instructions 1:

1.0 equivalent of the particular aromatic aldehyde compound of the general formula II was slowly added dropwise, while stirring at 20° C., to 2.7 equivalents of a 40% solution of the particular secondary amine with the general formula III. The solution was then subsequently stirred at a temperature of 80° C. for a further 30 minutes and then cooled to room temperature, and 0.57 equivalent of potassium carbonate was added. Two phases were formed here and were separated from one another, the aqueous phase being extracted three times with 100 ml ethyl acetate each time. The combined organic phases were dried over potassium carbonate and freed from the solvent. The aminal compounds of the general formula IV obtained in this way were then employed in the subsequent reactions without further purification.

General Synthesis Instructions 2:

1.6 equivalents of boric acid anhydride were added to a solution of 1.0 equivalent of the particular aromatic aldehyde compound of the general formula II in 80 ml absolute toluene. A solution of 2.4 equivalents of a secondary amine of the general formula III in 85 ml absolute toluene was then added with vigorous stirring. Starting of the reaction could be seen by a significant increase in temperature. The reaction solution was then subsequently stirred at a temperature of 45 to 50° C. for a further two hours. After cooling to room temperature the excess boric acid anhydride was separated off and the filtrate was freed from the solvent. The aminal compounds of the general formula IV obtained in this way were employed in the subsequent reactions without further purification.

General Synthesis Instructions for the Synthesis of Iminium Salts of the General Formula V:

General Synthesis Instructions 3:

A solution of 1.0 equivalent of acetyl chloride in absolute diethyl ether was slowly added dropwise, while stirring, to 1.0 equivalent of an ice-cooled solution or suspension of the aminal of the general formula III prepared in accordance with general synthesis instructions 1 or 2. The reaction mixture was then subsequently stirred overnight at approx. 20° C. A precipitate was formed here, and was filtered off with suction under nitrogen and then dried under an oil pump vacuum. The iminium salts of the general formula V obtained in this way were employed in the subsequent reactions without further purification.

Figure 2:
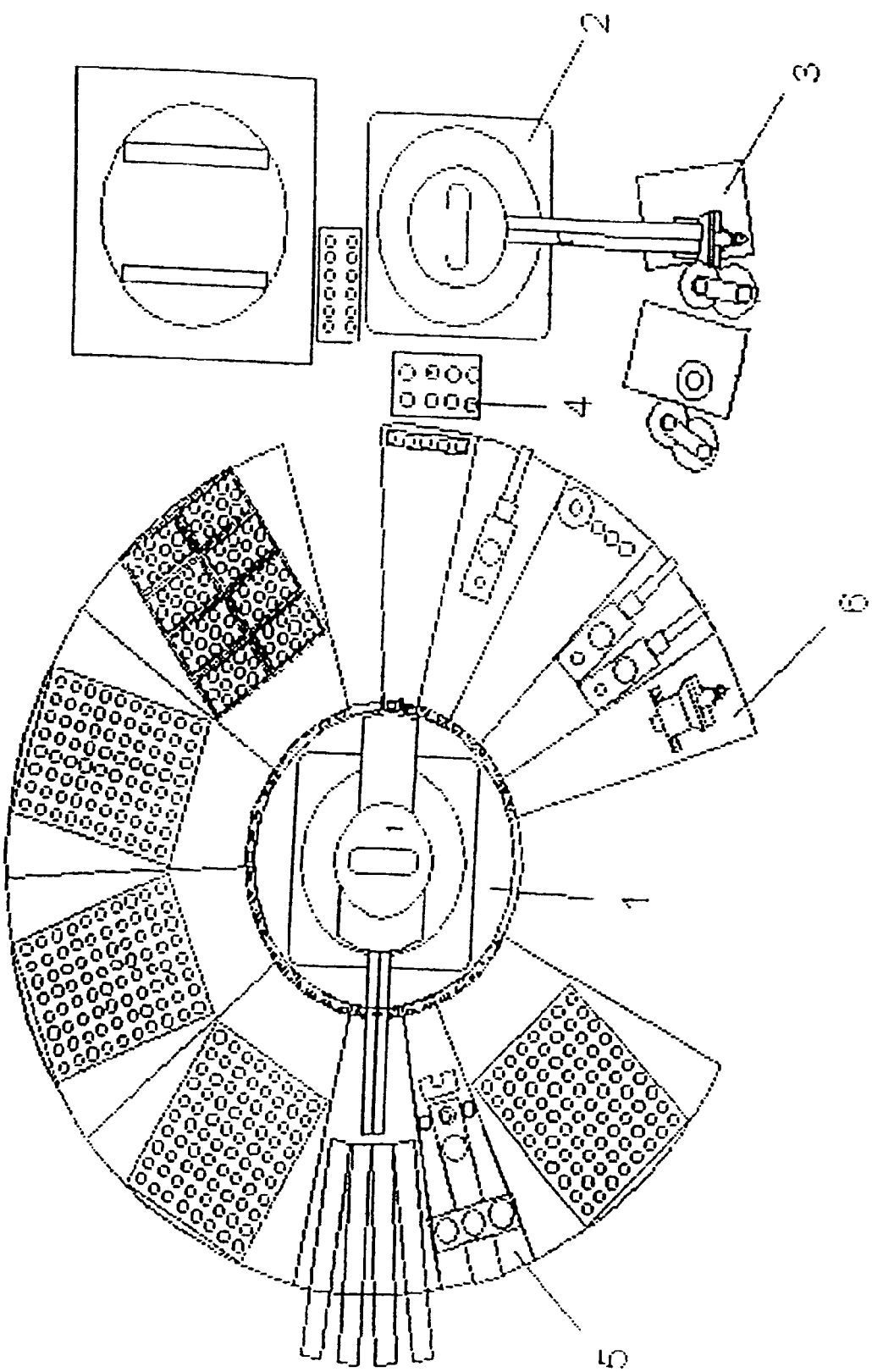

General Synthesis Instructions for the Synthesis of the Indole Mannich Bases of the General Formula I:

General Synthesis Instructions 4:

The synthesis of the indole Mannich bases according to the invention was carried out on an automatic unit from Zymark according to FIG. 1 and FIG. 2:

FIG. 1 here comprises a capper station (no. 1) for closing the reaction tubes, a robot 1 (no. 2) and a robot 2 (no. 3), robot 1 moving the reaction tubes and robot 2 pipetting the reagents into the reaction tubes, a temperature-controllable reactor block (no. 4), stirrer blocks (no. 5) and a filtration station (no. 6), in which the reaction solution is filtered.

FIG. 2 also comprises a robot 1 (no. 1) and a robot 2 (no. 2), the two robots bringing the vessels with the reaction products to the various stations at which the synthesis products from the automatic synthesis unit according to FIG. 1 are worked up.

Acetone is added here to the synthesis products on a vortexer (no. 3), the components are mixed thoroughly in a spin reactor (no. 4) and the acetone is then decanted off.

For the synthesis, a round-bottomed tube of glass (diameter 16 mm, length 125 mm) with a screw-thread was provided manually with a stirrer and closed with a screw-cap with a septum on the capper station (no. 1). The tube was placed by robot 1 (no. 2) in the reactor block, which was temperature-controlled at 0° C. Robot 2 (no. 3) pipetted in the following reagents in succession:

1.) 1 ml of a 0.1 M solution of indole or a substituted indole compound of the general formula VI in acetonitrile
2.) 1.2 ml of a 0.1 M solution of an iminium salt of the general formula V in acetonitrile The iminium salts were prepared beforehand as described in the following examples. Thereafter, the reaction mixture was stirred at 15° C. in one of the stirrer blocks (no. 5) for 665 min. The reaction solution was then filtered at the filtration station (no. 6).

The solvent was first removed in a vacuum centrifuge. The rack with the tubes was then placed manually on an automatic working-up unit (no. 3), FIG. 2. 2 ml acetone were added to the reaction mixture there on a vortexer. The components were mixed thoroughly in the spin reactor (no. 4) for 10 minutes, and finally the acetone was decanted off. This process was carried out a further three times and finally the solvent was removed in a vacuum centrifuge.

General Synthesis Instructions for the Synthesis of N-Alkylated Indole Mannich Bases of the General Formula I:

General Synthesis Instructions 5:

A solution of 1.0 equivalent of indole Mannich base of the general formula I where $R^1$=H in absolute dimethylsulfoxide was treated with 1.0 equivalent of potassium hydroxide for 15 minutes, 1.0 equivalent of alkylating reagent ($R^{12}$-Hal) was then added and the mixture was subsequently stirred at approx. 20° C. for a further 24 hours. 3.0 equivalents of 3-(3-mercaptophenyl)-propane-amidomethylpolystyrene were then added to this, the components were allowed to react with one another for a further three hours, the PS resin was filtered off and the filtrate was concentrated in vacuo. The residue obtained in this way was taken up in a 1:1 methylene chloride/water mixture, the mixture was stirred for 30 minutes and the phases were separated, the aqueous phase being extracted three times with 20 ml methylene chloride each time. The combined organic phases were dried over magnesium sulfate and freed from the solvent.

General Synthesis Instructions for the Synthesis of N-Acylated Indole Mannich Bases of the General Formula I:

General Synthesis Instructions 6:

A solution of 1.0 equivalent of indole Mannich base of the general formula I where $R^1$=H in absolute dimethylsulfoxide was treated with 1.0 equivalent of potassium hydroxide for 15 minutes, 1.0 equivalent of acylating reagent ($R^1$-Hal) was then added and the mixture was subsequently stirred at approx. 20° C. for a further 24 hours. 3.0 equivalents of polymer-bonded tris(2-aminoethyl)amine were then added to this, the components were allowed to react with one another for a further three hours, the PS resin was filtered off and the filtrate was concentrated in vacuo. The residue obtained in this way was taken up in a 1:1 methylene chloride/water mixture, the mixture was stirred for 30 minutes and the phases were separated, the aqueous phase being extracted three times with 20 ml methylene chloride each time. The combined organic phases were dried over magnesium sulfate and freed from the solvent.

Example 1

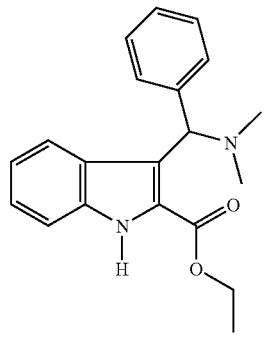

3-(Dimethylaminophenylmethyl)-1H-indole-2-carboxylic Acid Ethyl Ester

1st Stage

Benzylidene-dimethyl-ammonium Chloride

The reaction of 32.0 ml (0.213 mol) dimethylamine solution and 8.0 ml (0.079 mol) benzaldehyde in accordance with general synthesis instructions 1 and subsequent reaction with 4.7 ml (0.079 mol) acetyl chloride in accordance with general synthesis instructions 3 gave 9.5 g (corresponding to 70.7% of the yield calculated by theory) of benzylidene-dimethyl-ammonium chloride.

2nd Stage 3-(Dimethylaminophenylmethyl)-1H-indole-2-carboxylic Acid Ethyl Ester

The preparation was carried out in accordance with general synthesis instructions 4 from 1H-indole-2-carboxylic acid ethyl ester and benzylidene-dimethyl-ammonium chloride. For characterization, an ESI-MS was recorded:

MS (EI) m/z: 323.2, 278.4 (M*).

Example 2

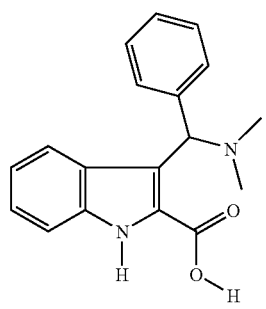

3-(Dimethylaminophenylmethyl)-1H-indole-2-carboxylic Acid

The preparation was carried out in accordance with general synthesis instructions 4 from 1H-indole-2-carboxylic acid and benzylidene-dimethyl-ammonium chloride, which had been prepared in accordance with example 1.

For characterization, an ESI-MS was recorded:
MS (EI) m/z: 295.2, 250.4, 206.6 (M*).

Example 3

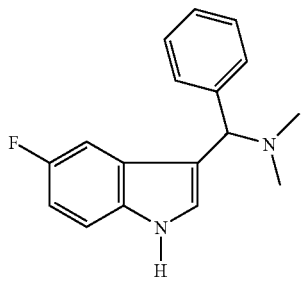

[(5-Fluoro-1H-indol-3-yl)-phenylmethyl]-dimethylamine

The preparation was carried out in accordance with general synthesis instructions 4 from 5-fluoro-1H-indole and benzylidene-dimethyl-ammonium chloride, which had been prepared in accordance with example 1.

For characterization, an ESI-MS was recorded:
MS (EI) m/z: 313.3, 268.3, 224.6 (M*).

Example 4

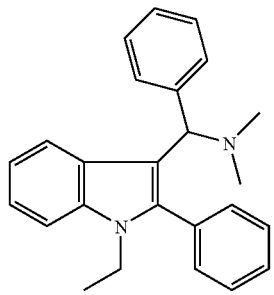

[(1-Ethyl-2-phenyl-1H-indol-3-yl)-phenylmethyl]-dimethylamine

The preparation was carried out in accordance with general synthesis instructions 4 from 1-ethyl-2-phenyl-1H-indole and benzylidene-dimethyl-ammonium chloride, which had been prepared in accordance with example 1.

For characterization, an ESI-MS was recorded:
MS (EI) m/z: 310.5 (M*).

Example 5

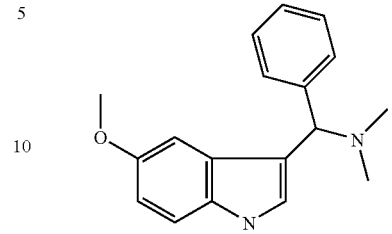

[(5-Methoxy-1H-indol-3-yl)-phenylmethyl]-dimethylamine

The preparation was carried out in accordance with general synthesis instructions 4 from 5-methoxy-1H-indole and benzylidene-dimethyl-ammonium chloride, which had been prepared in accordance with example 1.

For characterization, an ESI-MS was recorded:
MS (EI) m/z: 325.1, 280.3 (M*).

Example 6

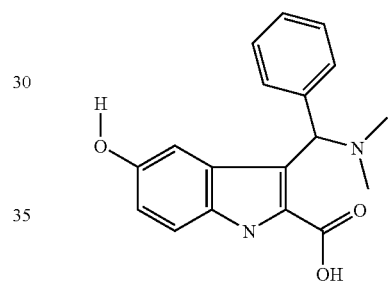

3-(Dimethylaminophenylmethyl)-5-hydroxy-1H-indole-2-carboxylic Acid

The preparation was carried out in accordance with general synthesis instructions 4 from 5-hydroxy-1H-indole-2-carboxylic acid and benzylidene-dimethyl-ammonium chloride, which had been prepared in accordance with example 1.

For characterization, an ESI-MS was recorded:
MS (EI) m/z: 310.6, 266.4, 222.5 (M*).

Example 7

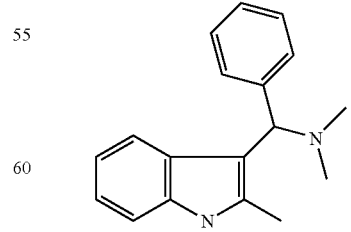

Dimethyl-[(2-methyl-1H-indol-3-yl)-phenylmethyl]-amine

The preparation was carried out in accordance with general synthesis instructions 4 from 2-methyl-1H-indole and benzylidene-dimethyl-ammonium chloride, which had been prepared in accordance with example 1.

For characterization, an ESI-MS was recorded:
MS (EI) m/z: 220.5 (M*).

Example 8

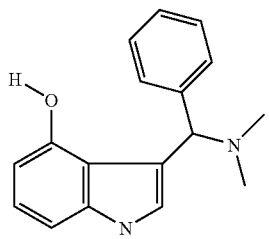

3-(Dimethylaminophenylmethyl)-1H-indol-4-ol

The preparation was carried out in accordance with general synthesis instructions 4 from 4-hydroxy-1H-indole and benzylidene-dimethyl-ammonium chloride, which had been prepared in accordance with example 1.

For characterization, an ESI-MS was recorded:
MS (EI) m/z: 267.1, 222.5 (M*).

Example 9

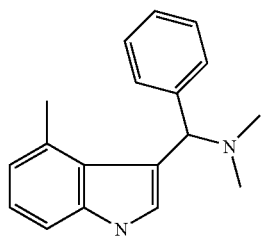

Dimethyl-[(4-methyl-1H-indol-3-yl)-phenylmethyl]-amine

The preparation was carried out in accordance with general synthesis instructions 4 from 4-methyl-1H-indole and benzylidene-dimethyl-ammonium chloride, which had been prepared in accordance with example 1.

For characterization, an ESI-MS was recorded:
MS (EI) m/z: 220.5 (M*).

Example 10

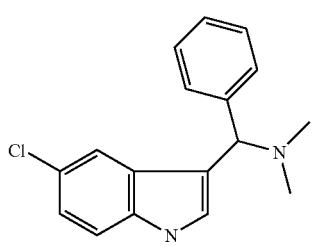

[(5-Chloro-1H-indol-3-yl)-phenylmethyl]-dimethylamine

The preparation was carried out in accordance with general synthesis instructions 4 from 5-chloro-1H-indole and benzylidene-dimethyl-ammonium chloride, which had been prepared in accordance with example 1.

For characterization, an ESI-MS was recorded:
MS (EI) m/z: 240.6 (M*).

Example 11

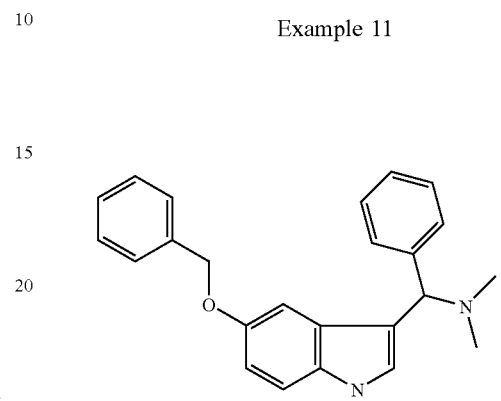

[(5-benzyloxy-1H-indol-3-yl)-phenylmethyl]-dimethylamine

The preparation was carried out in accordance with general synthesis instructions 4 from 5-benzyloxy-1H-indole and benzylidene-dimethyl-ammonium chloride, which had been prepared in accordance with example 1.

For characterization, an ESI-MS was recorded:
MS (EI) m/z: 312.4 (M*)

Example 12

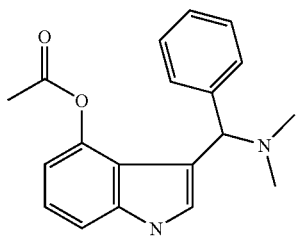

Acetic Acid 3-(dimethylaminophenylmethyl)-1H-indol-4-yl Ester

The preparation was carried out in accordance with general synthesis instructions 4 from acetic acid 1H-indol-4-yl ester and benzylidene-dimethyl-ammonium chloride, which had been prepared in accordance with example 1.

For characterization, an ESI-MS was recorded:
MS (EI) m/z: 264.3, 222.5 (M*).

Example 13

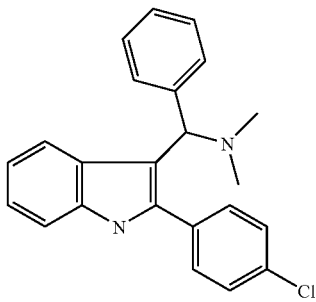

{[2-(4-Chlorophenyl)-1H-indol-3-yl]-phenylmethyl}-dimethylamine

The preparation was carried out in accordance with general synthesis instructions 4 from 2-(4-chlorophenyl)-1H-indole and benzylidene-dimethyl-ammonium chloride, which had been prepared in accordance with example 1.

For characterization, an ESI-MS was recorded:
MS (EI) m/z: 316.3 (M*).

Example 14

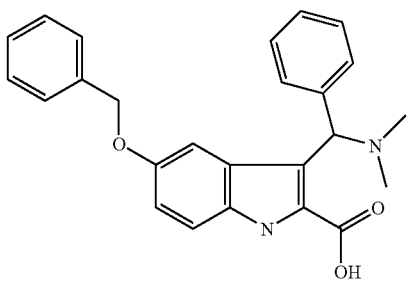

5-Benzyloxy-3-(dimethylaminophenylmethyl)-1H-indole-2-carboxylic Acid

The preparation was carried out in accordance with general synthesis instructions 4 from 5-benzyloxy-1H-indole-2-carboxylic acid and benzylidene-dimethyl-ammonium chloride, which had been prepared in accordance with example 1.

For characterization, an ESI-MS was recorded:
MS (EI) m/z: 401.1, 356.3, 312.4 (M*).

Example 15

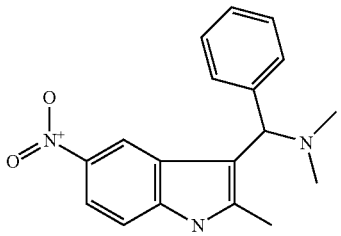

Dimethyl-[(2-methyl-5-nitro-1H-indol-3-yl)-phenylmethyl]-amine

The preparation was carried out in accordance with general synthesis instructions 4 from 2-methyl-5-nitro-1H-indole and benzylidene-dimethyl-ammonium chloride, which had been prepared in accordance with example 1.

For characterization, an ESI-MS was recorded:
MS (EI) m/z: 265.4, 235.6 (M*).

Example 16

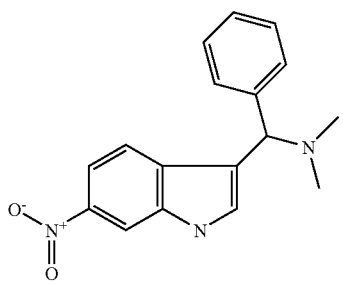

Dimethyl-[(6-nitro-1H-indol-3-yl)-phenylmethyl]-amine

The preparation was carried out in accordance with general synthesis instructions 4 from 6-nitro-1H-indole and benzylidene-dimethyl-ammonium chloride, which had been prepared in accordance with example 1.

For characterization, an ESI-MS was recorded:
MS (EI) m/z: 251.4 (M*)

Example 17

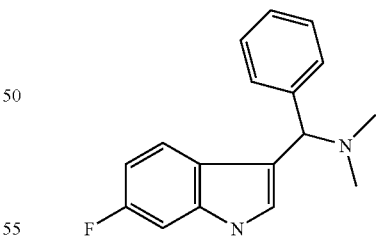

[(6-Fluoro-1H-indol-3-yl)-phenylmethyl]-dimethylamine

The preparation was carried out in accordance with general synthesis instructions 4 from 6-fluoro-1H-indole and benzylidene-dimethyl-ammonium chloride, which had been prepared in accordance with example 1.

For characterization, an ESI-MS was recorded:
MS (EI) m/z: 224.4 (M*).

Example 18

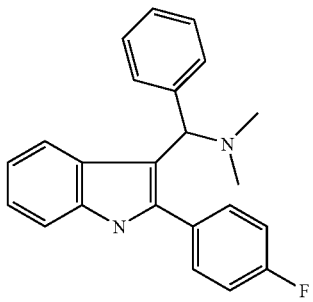

{[2-(4-Fluoro-phenyl)-1H-indol-3-yl]-phenylmethyl}-dimethylamine

The preparation was carried out in accordance with general synthesis instructions 4 from 2-(4-fluorophenyl)-1H-indole and benzylidene-dimethyl-ammonium chloride, which had been prepared in accordance with example 1.

For characterization, an ESI-MS was recorded:
MS (EI) m/z: 300.5, 224.5 (M*).

Example 19

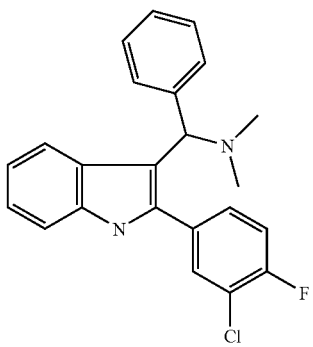

{[2-(3-Chloro-4-fluorophenyl)-1H-indol-3-yl]-phenylmethyl}-dimethylamine

The preparation was carried out in accordance with general synthesis instructions 4 from 2-(3-chloro-4-fluorophenyl)-1H-indole and benzylidene-dimethyl-ammonium chloride, which had been prepared in accordance with example 1.

For characterization, an ESI-MS was recorded:
MS (EI) m/z: 334.4 (M*).

Example 20

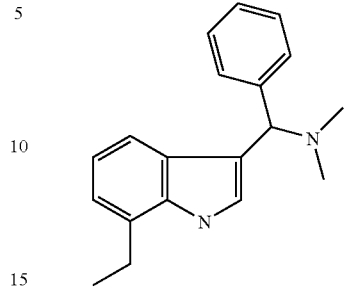

[(7-Ethyl-1H-indol-3-yl)-phenylmethyl]-dimethylamine

The preparation was carried out in accordance with general synthesis instructions 4 from 7-ethyl-1H-indole and benzylidene-dimethyl-ammonium chloride, which had been prepared in accordance with example 1.

For characterization, an ESI-MS was recorded:
MS (EI) m/z: 234.5 (M*).

Example 21

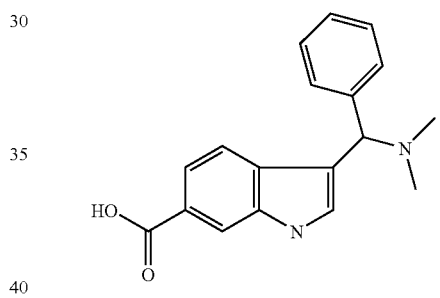

3-(Dimethylaminophenylmethyl)-1H-indole-6-carboxylic Acid

The preparation was carried out in accordance with general synthesis instructions 4 from 1H-indole-6-carboxylic acid and benzylidene-dimethyl-ammonium chloride, which had been prepared in accordance with example 1.

For characterization, an ESI-MS was recorded:
MS (EI) m/z: 264.4, 250.5 (M*).

Example 22

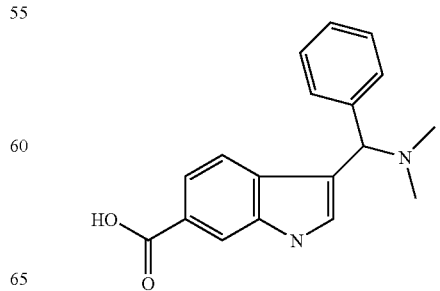

Dimethyl-[(1-methyl-1H-indol-3-yl)-phenylmethyl]-amine

The preparation was carried out in accordance with general synthesis instructions 4 from 1-methyl-1H-indole and benzylidene-dimethyl-ammonium chloride, which had been prepared in accordance with example 1.

For characterization, an ESI-MS was recorded:
MS (EI) m/z: 265.1 (M*).

Example 23

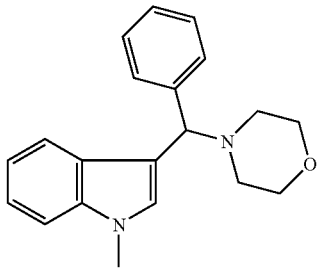

1-Methyl-3-(morpholin-4-yl-phenylmethyl)-1H-indole

1st Stage

4-Benzylidene-morpholin-4-ium Chloride

The reaction of 17.9 ml (0.200 mol) morpholine and 10.1 ml (0.100 mol) benzaldehyde in accordance with general synthesis instructions 2 and subsequent reaction with 6.0 ml (0.100 mol) acetyl chloride in accordance with general synthesis instructions 3 gave 10.1 g (corresponding to 48% of the yield calculated by theory) 4-benzylidene-morpholin-4-ium chloride.

2nd Stage

1-Methyl-3-(morpholin-4-yl-phenylmethyl)-1H-indole

The preparation was carried out in accordance with general synthesis instructions 4 from 1-methyl-1H-indole and 4-benzylidene-morpholin-4-ium chloride.

For characterization, an ESI-MS was recorded:
MS (EI) m/z: 220.4 (M*)

Example 24

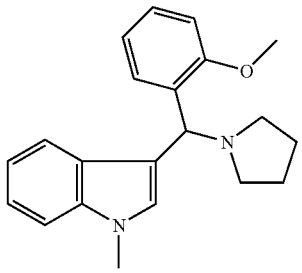

3-[(2-Methoxyphenyl)-pyrrolidin-1-yl-methyl]-1-methyl-1H-indole

1st Stage 1-(2-Methoxy-benzylidene)-pyrrolidinium Chloride

The reaction of 6.9 ml (0.084 mol) pyrrolidine and 4.8 g (0.035 mol) 2-methoxybenzaldehyde in accordance with general synthesis instructions 2 and subsequent reaction with 2.1 ml (0.035 mol) acetyl chloride in accordance with general synthesis instructions 3 gave 6.2 g (corresponding to 78% of the yield calculated by theory) 1-(2-methoxy-benzylidene)-pyrrolidinium chloride.

2nd Stage

3-[(2-Methoxyphenyl)-pyrrolidin-1-yl-methyl]-1-methyl-1H-indole

The preparation was carried out in accordance with general synthesis instructions 4 from 1-methyl-1H-indole and 1-(2-methoxy-benzylidene)-pyrrolidinium chloride.

For characterization, an ESI-MS was recorded:
MS (EI) m/z: 250.4 (M*).

Example 25

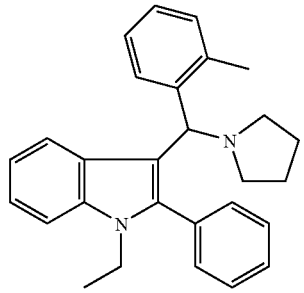

1-Ethyl-2-phenyl-3-(pyrrolidin-1-yl-o-tolylmethyl)-1H-indole

1st Stage 1-(2-Methyl-benzylidene)-pyrrolidinium Chloride

The reaction of 8.2 ml (0.100 mol) pyrrolidine and 7.0 g (0.050 mol) 2-methylbenzaldehyde in accordance with general synthesis instructions 2 and subsequent reaction with 3.9 g (0.050 mol) acetyl chloride in accordance with general synthesis instructions 3 gave 6.6 g (corresponding to 63% of the yield calculated by theory) 1-(2-methyl-benzylidene)-pyrrolidinium chloride.

2nd Stage

1-Ethyl-2-phenyl-3-(pyrrolidin-1-yl-o-tolylmethyl)-1H-indole

The preparation was carried out in accordance with general synthesis instructions 4 from 1-ethyl-2-phenyl-1H-indole and 1-(2-methyl-benzylidene)-pyrrolidinium chloride For characterization, an ESI-MS was recorded:
MS (EI) m/z: 324.4 (M*).

Example 26

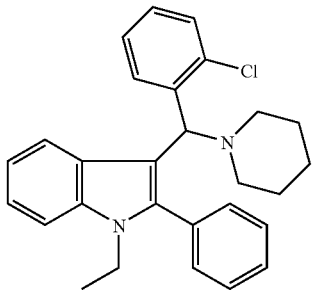

3-[(2-Chlorophenyl)-piperidin-1-yl-methyl]-1-ethyl-2-phenyl-1H-indole

1st Stage 1-(2-Chloro-benzylidene)-piperidinium Chloride

The reaction of 8.5 g (0.100 mol) piperidine and 7.0 g (0.050 mol) 2-chlorobenzaldehyde in accordance with general synthesis instructions 2 and subsequent reaction with 3.9 g (0.050 mol) acetyl chloride in accordance with general synthesis instructions 3 gave 7.1 g (corresponding to 58% of the yield calculated by theory) 1-(2-chloro-benzylidene)-piperidinium chloride.

2nd Stage

3-[(2-Chlorophenyl)-piperidin-1-yl-methyl]-1-ethyl-2-phenyl-1H-indole

The preparation was carried out in accordance with general synthesis instructions 4 from 1-ethyl-2-phenyl-1H-indole and 1-(2-chloro-benzylidene)-piperidinium chloride For characterization, an ESI-MS was recorded:

MS (EI) m/z: 344.4 (M*).

Example 27

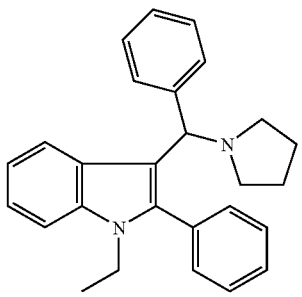

1-Ethyl-2-phenyl-3-(phenylpyrrolidin-1-yl-methyl)-1H-indole

1st Stage

1-Benzylidene-pyrrolidinium Chloride

The reaction of 16.4 ml (0.200 mol) pyrrolidine and 10.1 ml (0.100 mol) benzaldehyde in accordance with general synthesis instructions 2 and subsequent reaction with 6.0 ml (0.100 mol) acetyl chloride in accordance with general synthesis instructions 3 gave 14.1 g (corresponding to 72% of the yield calculated by theory) 1-benzylidene-pyrrolidinium chloride.

2nd Stage

1-Ethyl-2-phenyl-3-(phenylpyrrolidin-1-yl-methyl)-1H-indole

The preparation was carried out in accordance with general synthesis instructions 4 from 1-ethyl-2-phenyl-1H-indole and 1-benzylidene-pyrrolidinium chloride.

For characterization, an ESI-MS was recorded:

MS (EI) m/z: 310.5 (M*).

Example 28

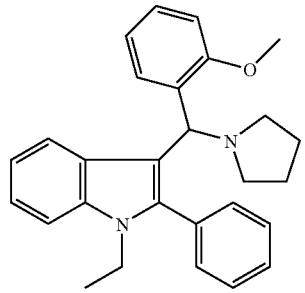

1-Ethyl-3-[(2-methoxyphenyl)-pyrrolidin-1-yl-methyl]-2-phenyl-1H-indole

The preparation was carried out in accordance with general synthesis instructions 4 from 1-ethyl-2-phenyl-1H-indole and 1-(2-methoxy-benzylidene)-pyrrolidinium chloride, which had been prepared in accordance with example 24.

For characterization, an ESI-MS was recorded:

MS (EI) m/z: 340.4 (M*)

Example 29

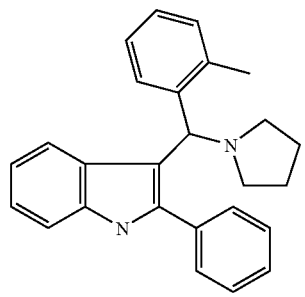

2-Phenyl-3-(pyrrolidin-1-yl-o-tolylmethyl)-1H-indole

The preparation was carried out in accordance with general synthesis instructions 4 from 2-phenyl-1H-indole and 1-(2-methyl-benzylidene)-pyrrolidinium chloride, which had been prepared in accordance with example 25.

For characterization, an ESI-MS was recorded:

MS (EI) m/z: 296.5 (M*)

Example 30

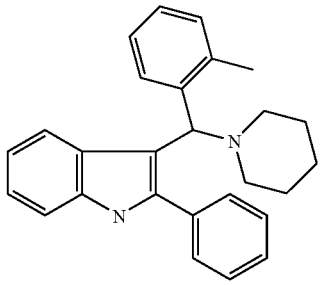

1st Stage

1-(2-Methyl-benzylidene)-piperidinium Chloride

The reaction of 9.5 ml (0.096 mol) piperidine and 4.7 ml (0.040 mol) 2-methylbenzaldehyde in accordance with general synthesis instructions 2 and subsequent reaction with 2.4 ml (0.040 mol) acetyl chloride in accordance with general synthesis instructions 3 gave 5.8 g (corresponding to 65% of the yield calculated by theory) 1-(2-methyl-benzylidene)-piperidinium chloride.

2nd Stage

2-Phenyl-3-(piperidin-1-yl-o-tolylmethyl)-1H-indole

The preparation was carried out in accordance with general synthesis instructions 4 from 2-phenyl-1H-indole and 1-(2-methyl-benzylidene)-piperidinium chloride.

For characterization, an ESI-MS was recorded:
MS (EI) m/z: 296.5 (M*).

Example 31

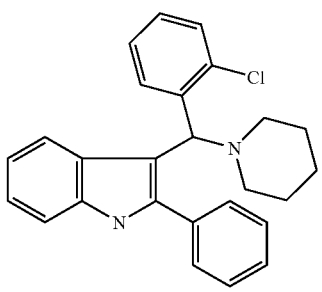

3-[(2-Chlorophenyl)-piperidin-1-yl-methyl]-2-phenyl-1H-indole

The preparation was carried out in accordance with general synthesis instructions 4 from 2-phenyl-1H-indole and 1-(2-chloro-benzylidene)-piperidinium chloride, which had been prepared in accordance with example 26.

For characterization, an ESI-MS was recorded:
MS (EI) m/z: 316.5 (M*).

Example 32

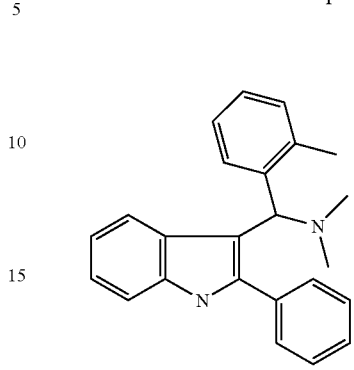

Dimethyl-[(2-phenyl-1H-indol-3-yl)-o-tolylmethyl]-amine

1st Stage

Dimethyl-(2-methyl-benzylidene)-ammonium Chloride

The reaction of 14.0 ml (0.108 mol) dimethylamine solution and 4.6 ml (0.040 mol) 2-methylbenzaldehyde in accordance with general synthesis instructions 1 and subsequent reaction with 2.4 ml (0.040 mol) acetyl chloride in accordance with general synthesis instructions 3 gave 5.3 g (corresponding to 73% of the yield calculated by theory) dimethyl-(2-methyl-benzylidene)-ammonium chloride.

2nd Stage

Dimethyl-[(2-phenyl-1H-indol-3-yl)-o-tolylmethyl]-amine

The preparation was carried out in accordance with general synthesis instructions 4 from 2-phenyl-1H-indole and dimethyl-(2-methyl-benzylidene)-ammonium chloride.

For characterization, an ESI-MS was recorded:
MS (EI) m/z: 296.6 (M*).

Example 33

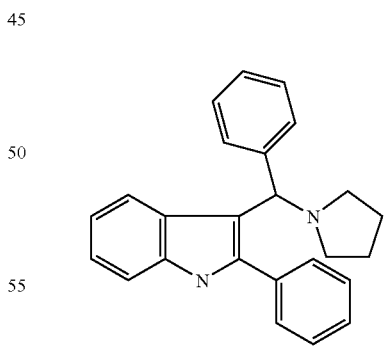

2-Phenyl-3-(phenylpyrrolidin-1-yl-methyl)-1H-indole

The preparation was carried out in accordance with general synthesis instructions 4 from 2-phenyl-1H-indole and 1-benzylidene-pyrrolidinium chloride, which had been prepared in accordance with example 27.

For characterization, an ESI-MS was recorded:
MS (EI) m/z: 282.5 (M*).

Example 34

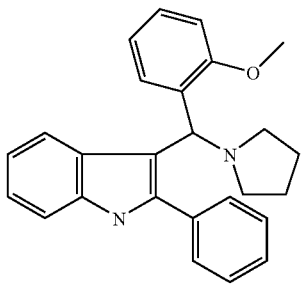

3-[(2-methoxyphenyl)-pyrrolidin-1-yl-methyl]-2-phenyl-1H-indole

The preparation was carried out in accordance with general synthesis instructions 4 from 2-phenyl-1H-indole and 1-(2-methoxy-benzylidene)-pyrrolidinium chloride, which had been prepared in accordance with example 24.

For characterization, an ESI-MS was recorded:
MS (EI) m/z: 312.3 (M*)

Example 35

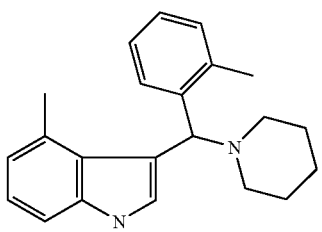

4-Methyl-3-(piperidin-1-yl-o-tolylmethyl)-1H-indole

The preparation was carried out in accordance with general synthesis instructions 4 from 4-methyl-1H-indole and 1-(2-methyl-benzylidene)-piperidinium chloride, which had been prepared in accordance with example 30.

For characterization, an ESI-MS was recorded:
MS (EI) m/z: 234.5 (M*).

Example 36

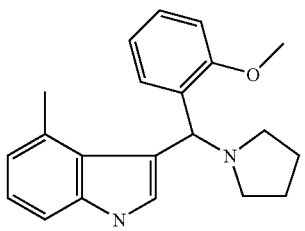

3-[(2-Methoxyphenyl)-pyrrolidin-1-yl-methyl]-4-methyl-1H-indole

The preparation was carried out in accordance with general synthesis instructions 4 from 4-methyl-1H-indole and 1-(2-methoxy-benzylidene)-pyrrolidinium chloride, which had been prepared in accordance with example 24.

For characterization, an ESI-MS was recorded:
MS (EI) m/z: 250.4 (M*).

Example 37

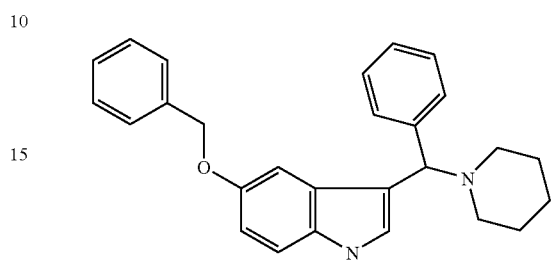

5-Benzyloxy-3-(phenylpiperidin-1-yl-methyl)-1H-indole

1st Stage

1-Benzylidene-piperidinium Chloride

The reaction of 19.8 ml (0.200 mol) piperidine and 10.1 ml (0.100 mol) benzaldehyde in accordance with general synthesis instructions 2 and subsequent reaction with 6.0 ml (0.100 mol) acetyl chloride in accordance with general synthesis instructions 3 gave 11.7 g (corresponding to 56% of the yield calculated by theory) 1-benzylidene-piperidinium chloride.

2nd Stage

5-Benzyloxy-3-(phenylpiperidin-1-yl-methyl)-1H-indole

The preparation was carried out in accordance with general synthesis instructions 4 from 5-benzyloxy-1H-indole and 1-benzylidene-piperidinium chloride.

For characterization, an ESI-MS was recorded:
MS (EI) m/z: 397.3, 312.5 (M*).

Example 38

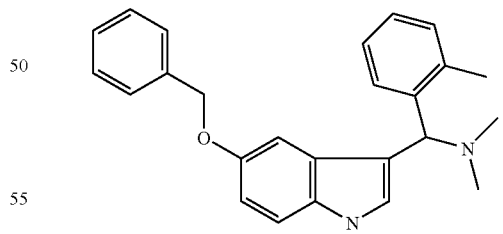

[(5-Benzyloxy-1H-indol-3-yl)-o-tolylmethyl]-dimethylamine

The preparation was carried out in accordance with general synthesis instructions 4 from 5-benzyloxy-1H-indole and dimethyl-(2-methyl-benzylidene)-ammonium chloride, which had been prepared in accordance with example 32.

For characterization, an ESI-MS was recorded:
MS (EI) m/z: 326.5 (M*).

Example 39

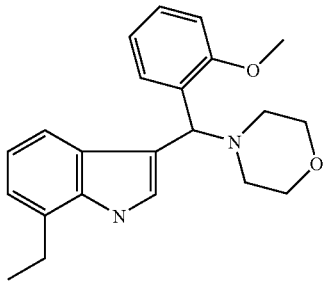

7-Ethyl-3-[(2-methoxyphenyl)-morpholin-4-yl-methyl]-1H-indole

1st Stage 4-(2-Methoxy-benzylidene)-morpholin-4-ium Chloride

The reaction of 18.8 ml (0.216 mol) morpholine and 12.4 g (0.09 mol) 2-methoxybenzaldehyde in accordance with general synthesis instructions 2 and subsequent reaction with 5.3 ml (0.110 mol) acetyl chloride in accordance with general synthesis instructions 3 gave 7.61 g (corresponding to 38% of the yield calculated by theory) 4-(2-methoxy-benzylidene)-morpholin-4-ium chloride.

2nd Stage

7-Ethyl-3-[(2-methoxyphenyl)-morpholin-4-yl-methyl]-1H-indole

The preparation was carried out in accordance with general synthesis instructions 4 from 7-ethyl-1H-indole and 4-(2-methoxy-benzylidene)-morpholin-4-ium chloride.

For characterization, an ESI-MS was recorded:

MS (EI) m/z: 264.3 (M*)

Example 40

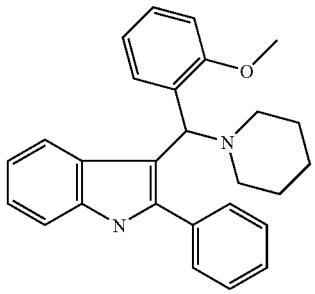

3-[(2-methoxyphenyl)-piperidin-1-yl-methyl]-2-phenyl-1H-indole

1st Stage 1-(2-Methoxy-benzylidene)-piperidinium Chloride

The reaction of 18.4 g (0.216 mol) piperidine and 25.9 g (0.090 mol) 2-methoxybenzaldehyde in accordance with general synthesis instructions 2 and subsequent reaction with 5.3 ml (0.11 mol) acetyl chloride in accordance with general synthesis instructions 3 gave 13.4 g (corresponding to 62% of the yield calculated by theory) 1-(2-methoxy-benzylidene)-piperidinium chloride.

2nd Stage

3-[(2-Methoxyphenyl)-piperidin-1-yl-methyl]-2-phenyl-1H-indole

The preparation was carried out in accordance with general synthesis instructions 4 from 2-phenyl-1H-indole and 1-(2-methoxy-benzylidene)-piperidinium chloride.

For characterization, an ESI-MS was recorded:

MS (EI) m/z: 312.3 (M*).

Example 41

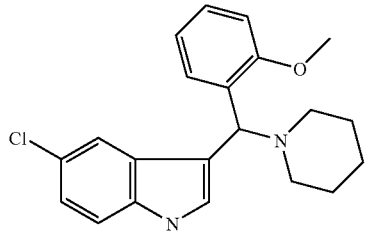

5-Chloro-3-[(2-methoxyphenyl)-piperidin-1-yl-methyl]-1H-indole

The preparation was carried out in accordance with general synthesis instructions 4 from 5-chloro-1H-indole and 1-(2-methoxy-benzylidene)-piperidinium chloride, which had been prepared in accordance with example 40.

For characterization, an ESI-MS was recorded:

MS (EI) m/z: 355.0, 270.3 (M*).

Example 42

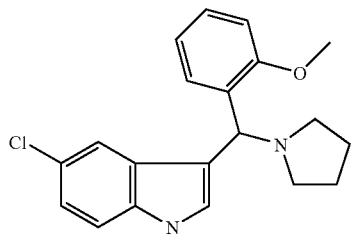

5-Chloro-3-[(2-methoxyphenyl)-pyrrolidin-1-yl-methyl]-1H-indole

The preparation was carried out in accordance with general synthesis instructions 4 from 5-chloro-1H-indole and 1-(2-methoxy-benzylidene)-pyrrolidinium chloride, which had been prepared in accordance with example 24.

For characterization, an ESI-MS was recorded:

MS (EI) m/z: 340.9, 270.2 (M*).

Example 43

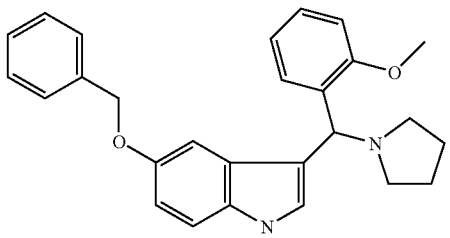

5-Benzyloxy-3-[(2-methoxyphenyl)-pyrrolidin-1-yl-methyl]-1H-indole

The preparation was carried out in accordance with general synthesis instructions 4 from 5-benzyloxy-1H-indole and 1-(2-methoxy-benzylidene)-pyrrolidinium chloride, which had been prepared in accordance with example 24.

For characterization, an ESI-MS was recorded:
MS (EI) m/z: 412.9, 342.3 (M*).

Example 44

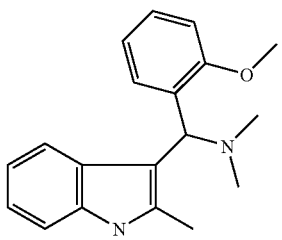

[(2-Methoxyphenyl)-(2-methyl-1H-indol-3-yl)-methyl]-dimethylamine

1st Stage (2-Methoxy-benzylidene)-dimethyl-ammonium Chloride

The reaction of 17.0 ml (0.135 mol) dimethylamine solution and 6.8 g ml (0.050 mol) 2-methoxybenzaldehyde in accordance with general synthesis instructions 1 and subsequent reaction with 3.0 ml (0.050 mol) acetyl chloride in accordance with general synthesis instructions 3 gave 4.8 g (corresponding to 48% of the yield calculated by theory) 2-methoxy-benzylidene-dimethyl-ammonium chloride.

2nd Stage

[(2-Methoxyphenyl)-(2-methyl-1H-indol-3-yl)-methyl]-dimethylamine

The preparation was carried out in accordance with general synthesis instructions 4 from 2-methyl-1H-indole and (2-methoxy-benzylidene)-dimethyl-ammonium chloride.

For characterization, an ESI-MS was recorded:
MS (EI) m/z: 250.3 (M*).

Example 45

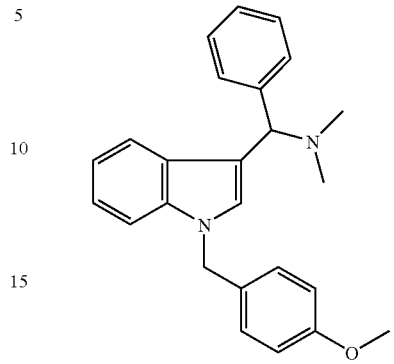

{[1-(4-Methoxybenzyl)-1H-indol-3-yl]-phenylmethyl}-dimethylamine

The preparation was carried out in accordance with general synthesis instructions 4 and 5 from 1H-indole, benzylidene-dimethyl-ammonium chloride and 4-methoxybenzyl chloride For characterization, an ESI-MS was recorded:
MS (EI) m/z: 327.1 (M*).

Example 46

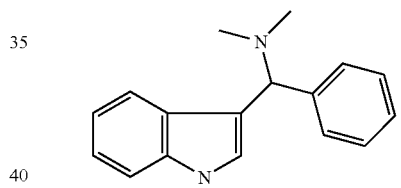

[(1H-Indol-3-yl)-phenylmethyl]-dimethylamine

The preparation was carried out in accordance with general synthesis instructions 4 from 1H-indole and benzylidene-dimethyl-ammonium chloride, which had been prepared in accordance with example 1.

The structure was demonstrated by means of: $^{13}$C-NMR, δ=144.35; 136.73; 128.30; 127.89; 126.55; 126.28; 123.32; 121.20; 119.96; 118.75; 111.72; 69.67; 44.49 ppm.

Example 47

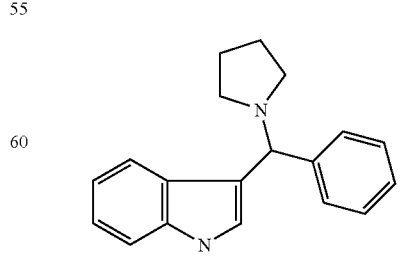

3-(Phenylpyrrolidin-1-yl-methyl)-1H-indole

The preparation was carried out in accordance with general synthesis instructions 4 from 1H-indole and 1-benzylidene-pyrrolidinium chloride, which had been prepared in accordance with example 27.

The structure was demonstrated by means of ESI-MS: mass calculated 276.38 g/mol, mass found M+H=276.9 g/mol.

Example 48

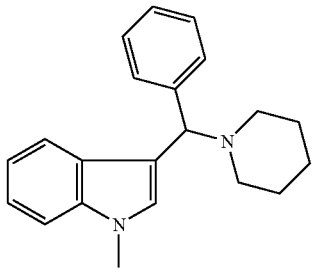

1-Methyl-3-(phenylpiperidin-1-yl-methyl)-1H-indole

The preparation was carried out in accordance with general synthesis instructions 4 from 1-methyl-1H-indole and 1-benzylidene-piperidinium chloride, which had been prepared in accordance with example 37.

The structure was demonstrated by means of ESI-MS: mass calculated 304.44 g/mol, mass found M+H=304.8 g/mol.

Example 49

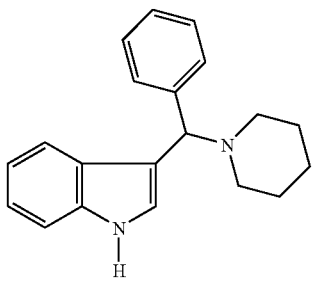

3-(Phenylpiperidin-1-yl-methyl)-1H-indole

The preparation was carried out in accordance with general synthesis instructions 4 from 1H-indole and 1-benzylidene-piperidinium chloride, which had been prepared in accordance with example 37.

The structure was demonstrated by means of ESI-MS: mass calculated 290.41 g/mol, mass found M+H=290.9 g/mol.

Example 50

5-Benzyloxy-3-(phenyl-pyrrolidin-yl-methyl)-1H-indole

The preparation was carried out in accordance with general synthesis instructions 4 from 5-benzyloxyindole and benzylidene-pyrrolidinium chloride, which had been prepared in accordance with example 27.

Example 51

[(5-Bromo-2-fluoro-phenyl)-(4-nitro-1H-indol-3-yl)-methyl]-dimethyl-amine

The preparation was carried out in accordance with general synthesis instructions 4 from 4-nitroindole and (5-bromo-2-fluoro-benzylidene)-dimethyl-ammonium chloride, which had been prepared in accordance with example 24 from 5-bromo-2-fluoro-benzaldehyde and dimethylamine.

Example 52

[(5-Bromo-2-fluoro-phenyl)-(1-methyl-1H-indol-3-yl)-methyl]-dimethyl-amine

The preparation was carried out in accordance with general synthesis instructions 4 from 1-methylindole and (5-bromo-2-fluoro-benzylidene)-dimethyl-ammonium chloride, which had been prepared in accordance with example 24 from 5-bromo-2-fluoro-benzaldehyde and dimethylamine.

Example 53

[(2-Chloro-6-fluoro-phenyl)-(2-phenyl-1H-indol-3-yl)-methyl]-dimethylamine

The preparation was carried out in accordance with general synthesis instructions 4 from 2-phenylindole and (2-chloro-6-fluoro-benzylidene)-dimethyl-ammonium chloride, which had been prepared in accordance with example 24 from 2-chloro-6-fluoro-benzaldehyde and dimethylamine.

Example 54

[(2-Chloro-6-fluoro-phenyl)-(1-ethyl-2-phenyl-1H-indol-3-yl)-methyl]-dimethylamine The preparation was carried out in accordance with general synthesis instructions 4 from 1-ethylindole and (2-chloro-6-fluoro-benzylidene)-dimethyl-ammonium chloride, which had been prepared in accordance with example 24 from 2-chloro-6-fluoro-benzaldehyde and dimethylamine.

Example 55

[(2-Chloro-6-fluoro-phenyl)-(4-nitro-1H-indol-3-yl)-methyl]-dimethyl-amine

The preparation was carried out in accordance with general synthesis instructions 4 from 4-nitroindole and (2-chloro-6-fluoro-benzylidene)-dimethyl-ammonium chloride, which had been prepared in accordance with example 24 from 2-chloro-6-fluoro-benzaldehyde and dimethylamine.

Example 56

[(2-Chloro-6-fluoro-phenyl)-(1-methyl-1H-indol-3-yl)-methyl]-dimethyl-amine

The preparation was carried out in accordance with general synthesis instructions 4 from 1-methylindole and (2-chloro-6-fluoro-benzylidene)-dimethyl-ammonium chloride, which had been prepared in accordance with example 24 from 2-chloro-6-fluoro-benzaldehyde and dimethylamine.

Example 57

[(2-Bromo-phenyl)-(4-nitro-1H-indol-3-yl)-methyl]-dimethyl-amine

The preparation was carried out in accordance with general synthesis instructions 4 from 4-nitroindole and (2-bromo-benzylidene)-dimethyl-ammonium chloride, which had been prepared in accordance with example 24 from 2-bromo-benzaldehyde and dimethylamine.

Example 58

[(2-Bromo-phenyl)-(1-methyl-1H-indol-3-yl)-methyl]-dimethyl-amine

The preparation was carried out in accordance with general synthesis instructions 4 from 1-methylindole and (2-bromo-benzylidene)-dimethyl-ammonium chloride, which had been prepared in accordance with example 24 from 2-bromo-benzaldehyde and dimethylamine.

Example 59

[(3-Bromo-phenyl)-(7-ethyl-1H-indol-3-yl)-methyl]-dimethyl-amine

The preparation was carried out in accordance with general synthesis instructions 4 from 7-ethylindole and (3-bromo-benzylidene)-dimethyl-ammonium chloride, which had been prepared in accordance with example 24 from 3-bromo-benzaldehyde and dimethylamine.

Example 60

[(3-Bromo-phenyl)-(1-methyl-1H-indol-3-yl)-methyl]-dimethyl-amine

The preparation was carried out in accordance with general synthesis instructions 4 from 1-methylindole and (3-bromo-benzylidene)-dimethyl-ammonium chloride, which had been prepared in accordance with example 24 from 3-bromo-benzaldehyde and dimethylamine.

Example 61

[(4-tert-Butyl-phenyl)-(2-methyl-1H-indol-3-yl)-methyl]-dimethyl-amine

The preparation was carried out in accordance with general synthesis instructions 4 from 2-methylindole and (4-tert-butyl-benzylidene)-dimethyl-ammonium chloride, which had been prepared in accordance with example 24 from 4-tert-butyl-benzaldehyde and dimethylamine.

Example 62

[(4-tert-Butyl-phenyl)-(1-ethyl-2-phenyl-1H-indol-3-yl)-methyl]-dimethyl-amine

The preparation was carried out in accordance with general synthesis instructions 4 from 1-ethyl-2-phenylindole and (4-tert-butyl-benzylidene)-dimethyl-ammonium chloride, which had been prepared in accordance with example 24 from 4-tert-butyl-benzaldehyde and dimethylamine.

Example 63

[(4-tert-Butyl-phenyl)-(1-methyl-1H-indol-3-yl)-methyl]-dimethyl-amine

The preparation was carried out in accordance with general synthesis instructions 4 from 1-methylindole and (4-tert-butyl-benzylidene)-dimethyl-ammonium chloride, which had been prepared in accordance with example 24 from 4-tert-butyl-benzaldehyde and dimethylamine.

Example 64

[(2-Chloro-4-fluoro-phenyl)-(4-nitro-1H-indol-3-yl)-methyl]-dimethyl-amine

The preparation was carried out in accordance with general synthesis instructions 4 from 4-nitroindole and (2-chloro-4-fluoro-benzylidene)-dimethyl-ammonium chloride, which had been prepared in accordance with example 24 from 2-chloro-4-fluoro-benzaldehyde and dimethylamine.

Example 65

[(2-Chloro-4-fluoro-phenyl)-(4-methyl-1H-indol-3-yl)-methyl]-dimethyl-amine

The preparation was carried out in accordance with general synthesis instructions 4 from 4-methylindole and (2-chloro-4-fluoro-benzylidene)-dimethyl-ammonium chloride, which had been prepared in accordance with example 24 from 2-chloro-4-fluoro-benzaldehyde and dimethylamine.

Example 66

[(2-Chloro-6-fluoro-phenyl)-(2-phenyl-1H-indol-3-yl)-methyl]-dimethyl-amine

The preparation was carried out in accordance with general synthesis instructions 4 from 2-phenylindole and (2-chloro-6-fluoro-benzylidene)-dimethyl-ammonium chloride, which had been prepared in accordance with example 24 from 2-chloro-6-fluoro-benzaldehyde and dimethylamine.

Example 67

{(2-Chloro-6-fluoro-phenyl)-[2-(4-chloro-phenyl)-1H-indol-3-yl]-methyl}-dimethyl-amine The preparation was carried out in accordance with general synthesis instructions 4 from 2-(4-chlorophenyl)-indole and (2-chloro-6-fluoro-benzylidene)-dimethyl-ammonium chloride, which had been prepared in accordance with example 24 from 2-chloro-6-fluoro-benzaldehyde and dimethylamine.

Example 68

[(2-Chloro-6-fluoro-phenyl)-(1-methyl-1H-indol-3-yl)-methyl]-dimethyl-amine

The preparation was carried out in accordance with general synthesis instructions 4 from 1-methylindole and (2-chloro-6-fluoro-benzylidene)-dimethyl-ammonium chloride, which had been prepared in accordance with example 24 from 2-chloro-6-fluoro-benzaldehyde and dimethylamine.

Example 69

[(3-Chloro-phenyl)-(1-methyl-1H-indol-3-yl)-methyl]-dimethyl-amine

The preparation was carried out in accordance with general synthesis instructions 4 from 1-methylindole and (3-chloro-benzylidene)-dimethyl-ammonium chloride, which had been prepared in accordance with example 24 from 3-chloro-benzaldehyde and dimethylamine.

Example 70

[(2,3-Dichloro-phenyl)-(1-methyl-1H-indol-3-yl)-methyl]-dimethyl-amine

The preparation was carried out in accordance with general synthesis instructions 4 from 1-methylindole and (2,3-dichloro-benzylidene)-dimethyl-ammonium chloride, which had been prepared in accordance with example 24 from 2,3-dichloro-benzaldehyde and dimethylamine.

Example 71

[(2,4-Dichloro-phenyl)-(1-methyl-1H-indol-3-yl)-methyl]-dimethyl-amine

The preparation was carried out in accordance with general synthesis instructions 4 from 1-methylindole and (2,4-dichloro-benzylidene)-dimethyl-ammonium chloride, which had been prepared in accordance with example 24 from 2,4-dichloro-benzaldehyde and dimethylamine.

Example 72

[(4-tert-Butyl-phenyl)-(1-ethyl-2-phenyl-1H-indol-3-yl)-methyl]-dimethyl-amine

The preparation was carried out in accordance with general synthesis instructions 4 from 1-ethyl-2-phenyl-1H-indole and (4-tert-butyl-benzylidene)-dimethylammonium chloride, which had been prepared in accordance with example 44 from 4-tert-butylbenzaldehyde and dimethylamine.

Example 73

[(2-Chloro-4-fluoro-phenyl)-(2-methyl-1H-indol-3-yl)-methyl]-dimethyl-amine

The preparation was carried out in accordance with general synthesis instructions 4 from 2-methyl-1H-indole and (2-chloro-4-fluoro-benzylidene)-dimethylammonium chloride, which had been prepared in accordance with example 44 from 2-chloro-4-fluoro-benzaldehyde and dimethylamine.

Example 74

[(2-Chloro-6-fluoro-phenyl)-(2-methyl-1H-indol-3-yl)-methyl]-dimethyl-amine

The preparation was carried out in accordance with general synthesis instructions 4 from 2-methyl-1H-indole and (2-chloro-6-fluoro-benzylidene)-dimethylammonium chloride, which had been prepared in accordance with example 44 from 2-chloro-6-fluoro-benzaldehyde and dimethylamine.

Example 75

[(2,3-Dimethoxy-phenyl)-(4-nitro-1H-indol-3-yl)-methyl]-dimethylamine

The preparation was carried out in accordance with general synthesis instructions 4 from 4-nitro-1H-indole and (2,3-dimethoxy-benzylidene)-dimethylammonium chloride, which had been prepared in accordance with example 44 from 2,3-dimethoxy-benzaldehyde and dimethylamine.

Example 76

3-[(2,3-Dimethoxy-phenyl)-dimethylamino-methyl]-4,7-dihydro-1H-indole-6-carboxylic Acid The preparation was carried out in accordance with general synthesis instructions 4 from 1H-indole-6-carboxylic acid and (2,3-dimethoxy-benzylidene)-dimethylammonium chloride, which had been prepared in accordance with example 44 from 2,3-dimethoxy-benzaldehyde and dimethylamine.

Example 77

3-[(2,3-Dimethoxy-phenyl)-dimethylamino-methyl]-5-hydroxy-1H-indole-2-carboxylic Acid The preparation was carried out in accordance with general synthesis instructions 4 from 1H-indole-5-hydoxy-2-carboxylic acid and (2,3-dimethoxy-benzylidene)-dimethylammonium chloride, which had been prepared in accordance with example 44 from 2,3-dimethoxy-fluoro-benzaldehyde and dimethylamine.

Example 78

[(3,4-Dimethoxy-phenyl)-(2-methyl-1H-indol-3-yl)-methyl]-dimethyl-amine

The preparation was carried out in accordance with general synthesis instructions 4 from 2-methyl-1H-indole and (3,4-dimethoxy-benzylidene)-dimethylammonium chloride, which had been prepared in accordance with example 44 from 3,4-dimethoxy-benzaldehyde and dimethylamine.

Example 79

[[2-(4-Chloro-phenyl)-1H-indol-3-yl]-(3,4-dimethoxy-phenyl)-methyl]-dimethyl-amine The preparation was carried out in accordance with general synthesis instructions 4 from 2-(4-chloro-phenyl)-1H-indole and (3,4-dimethoxy-benzylidene)-dimethylammonium chloride, which had been prepared in accordance with example 44 from 3,4-dimethoxy-benzaldehyde and dimethylamine.

Example 80

[(3,4-Dimethoxy-phenyl)-(1-ethyl-2-phenyl-1H-indol-3-yl)-methyl]-dimethyl-amine

The preparation was carried out in accordance with general synthesis instructions 4 from 1-ethyl-2-phenyl-1H-indole and (3,4-dimethoxy-benzylidene)-dimethylammonium chloride, which had been prepared in accordance with example 44 from 3,4-dimethoxy-benzaldehyde and dimethylamine.

Example 81

[(3,4-Dimethoxy-phenyl)-(7-ethyl-1H-indol-3-yl)-methyl]-dimethyl-amine

The preparation was carried out in accordance with general synthesis instructions 4 from 7-ethyl-1H-indole and (3,4-dimethoxy-benzylidene)-dimethylammonium chloride, which had been prepared in accordance with example 44 from 3,4-dimethoxy-benzaldehyde and dimethylamine.

Example 82

[(3,4-Dimethoxy-phenyl)-(1-methyl-1H-indol-3-yl)-methyl]-dimethyl-amine

The preparation was carried out in accordance with general synthesis instructions 4 from 1-methyl-1H-indole and (3,4-dimethoxy-benzylidene)-dimethylammonium chloride, which had been prepared in accordance with example 44 from 3,4-dimethoxy-benzaldehyde and dimethylamine.

Example 83

[(3,4-Dimethoxy-phenyl)-[2-(4-fluoro-phenyl)-1H-indol-3-yl]-methyl]-dimethylamine The preparation was carried out in accordance with general synthesis instructions 4 from 2-(4-fluoro-phenyl)-1H-indole and (3,4-dimethoxy-benzylidene)-dimethylammonium chloride, which had been prepared in accordance with example 44 from 3,4-dimethoxy-benzaldehyde and dimethylamine.

Example 84

[[2-(3-Chloro-4-fluoro-phenyl)-1H-indol-3-yl]-(3,4-dimethoxy-phenyl)-methyl]-dimethyl-amine The preparation was carried out in accordance with general synthesis instructions 4 from 2-(3-chloro-4-fluoro-phenyl)-1H-indole and (3,4-dimethoxy-benzylidene)-dimethylammonium chloride, which had been prepared in accordance with example 44 from 3,4-dimethoxy-benzaldehyde and dimethylamine.

Example 85

[(5-Chloro-1H-indol-3-yl)-(2-fluoro-phenyl)-methyl]-dimethyl-amine

The preparation was carried out in accordance with general synthesis instructions 4 from 5-chloro-1H-indole and (2-fluoro-benzylidene)-dimethylammonium chloride, which had been prepared in accordance with example 44 from 2-fluoro-benzaldehyde and dimethylamine.

Example 86

[(4-Fluoro-phenyl)-(4-methyl-1H-indol-3-yl)-methyl]-dimethyl-amine

The preparation was carried out in accordance with general synthesis instructions 4 from 4-methyl-1H-indole and (4-fluoro-benzylidene)-dimethylammonium chloride, which had been prepared in accordance with example 44 from 4-fluoro-benzaldehyde and dimethylamine.

Example 87

[(7-Ethyl-1H-indol-3-yl)-(2-methoxy-phenyl)-methyl]-dimethyl-amine

The preparation was carried out in accordance with general synthesis instructions 4 from 7-ethyl-1H-indole and (2-methoxy-benzylidene)-dimethylammonium chloride, which had been prepared in accordance with example 44 from 2-methoxy-benzaldehyde and dimethylamine.

Example 88

Dimethyl-[(2-methyl-1H-indol-3-yl)-o-tolyl-methyl]-amine

The preparation was carried out in accordance with general synthesis instructions 4 from 2-methyl-1H-indole and (2-methyl-benzylidene)-dimethylammonium chloride, which had been prepared in accordance with example 44 from 2-methyl-benzaldehyde and dimethylamine.

Example 89

[(7-Ethyl-1H-indol-3-yl)-o-tolyl-methyl]-dimethyl-amine

The preparation was carried out in accordance with general synthesis instructions 4 from 7-ethyl-1H-indole and (2-methyl-benzylidene)-dimethylammonium chloride, which had been prepared in accordance with example 44 from 2-methyl-benzaldehyde and dimethylamine.

Example 90

Dimethyl-[(1-methyl-1H-indol-3-yl)-o-tolyl-methyl]-amine

The preparation was carried out in accordance with general synthesis instructions 4 from 1-methyl-1H-indole and (2-methyl-benzylidene)-dimethylammonium chloride, which had been prepared in accordance with example 44 from 2-methyl-benzaldehyde and dimethylamine.

Example 91

[(5-Chloro-1H-indol-3-yl)-o-tolyl-methyl]-dimethyl-amine

The preparation was carried out in accordance with general synthesis instructions 4 from 5-chloro-1H-indole and (2-methyl-benzylidene)-dimethylammonium chloride, which had been prepared in accordance with example 44 from 2-methyl-benzaldehyde and dimethylamine.

Example 92

[(5-Chloro-1H-indol-3-yl)-m-tolyl-methyl]-dimethyl-amine

The preparation was carried out in accordance with general synthesis instructions 4 from 5-chloro-1H-indole and (3-methyl-benzylidene)-dimethylammonium chloride, which had been prepared in accordance with example 44 from 3-methyl-benzaldehyde and dimethylamine.

Example 93

Dimethyl-[(2-methyl-1H-indol-3-yl)-p-tolyl-methyl]-amine

The preparation was carried out in accordance with general synthesis instructions 4 from 2-methyl-1H-indole and (4-methyl-benzylidene)-dimethylammonium chloride, which had been prepared in accordance with example 44 from 4-methyl-benzaldehyde and dimethylamine.

Example 94

[(5-Chloro-1H-indol-3-yl)-p-tolyl-methyl]-dimethyl-amine

The preparation was carried out in accordance with general synthesis instructions 4 from 5-chloro-1H-indole and (4-methyl-benzylidene)-dimethylammonium chloride, which had been prepared in accordance with example 44 from 4-methyl-benzaldehyde and dimethylamine.

Example 95

Dimethyl-[(2-methyl-1H-indol-3-yl)-(3-phenoxy-phenyl)-methyl]-amine

The preparation was carried out in accordance with general synthesis instructions 4 from 2-methyl-1H-indole and (3-phenoxy-benzylidene)-dimethylammonium chloride, which had been prepared in accordance with example 44 from 3-phenoxy-benzaldehyde and dimethylamine.

Example 96

[(1-Ethyl-2-phenyl-1H-indol-3-yl)-(3-phenoxy-phenyl)-methyl]-dimethylamine

The preparation was carried out in accordance with general synthesis instructions 4 from 1-ethyl-2-phenyl-1H-indole and (3-phenoxy-benzylidene)-dimethylammonium chloride, which had been prepared in accordance with example 44 from 3-phenoxy-benzaldehyde and dimethylamine.

Example 97

[(7-Ethyl-1H-indol-3-yl)-(3-phenoxy-phenyl)-methyl]-dimethyl-amine

The preparation was carried out in accordance with general synthesis instructions 4 from 7-ethyl-1H-indole and (3-phenoxy-benzylidene)-dimethylammonium chloride, which had been prepared in accordance with example 44 from 3-phenoxy-benzaldehyde and dimethylamine.

Example 98

Dimethyl-[(1-methyl-1H-indol-3-yl)-(3-phenoxy-phenyl)-methyl]-amine

The preparation was carried out in accordance with general synthesis instructions 4 from 1-methyl-1H-indole and (3-phenoxy-benzylidene)-dimethylammonium chloride, which had been prepared in accordance with example 44 from 3-phenoxy-benzaldehyde and dimethylamine.

Example 99

[[2-(4-Fluoro-phenyl)-1H-indol-3-yl]-(3-phenoxy-phenyl)-methyl]-dimethyl-amine

The preparation was carried out in accordance with general synthesis instructions 4 from 2-(4-fluoro-phenyl)-1H-indole and (3-phenoxy-benzylidene)-dimethylammonium chloride, which had been prepared in accordance with example 44 from 3-phenoxy-benzaldehyde and dimethylamine.

Example 100

[[2-(3-Chloro-4-fluoro-phenyl)-1H-indol-3-yl]-(3-phenoxy-phenyl)-methyl]-amine

The preparation was carried out in accordance with general synthesis instructions 4 from 2-(3-chloro-4-fluoro-phenyl)-methyl-1H-indole and (3-phenoxy-benzylidene)-dimethylammonium chloride, which had been prepared in accordance with example 44 from 3-phenoxy-benzaldehyde and dimethylamine.

Example 101

Dimethyl-[(4-methyl-1H-indol-3-yl)-(3-phenoxy-phenyl)-methyl]-amine

The preparation was carried out in accordance with general synthesis instructions 4 from 4-methyl-1H-indole and (3-phenoxy-benzylidene)-dimethylammonium chloride, which had been prepared in accordance with example 44 from 3-phenoxy-benzaldehyde and dimethylamine.

Example 102

[(5-Chloro-1H-indol-3-yl)-(2-trifluoromethyl-phenyl)-methyl]-dimethyl-amine

The preparation was carried out in accordance with general synthesis instructions 4 from 5-chloro-1H-indole and (2-trifluoromethyl-benzylidene)-dimethylammonium chloride, which had been prepared in accordance with example 44 from 2-trifluoromethyl-benzaldehyde and dimethylamine.

Example 103

Dimethyl-[(2-methyl-1H-indol-3-yl)-(4-trifluoromethyl-phenyl)-methyl]-amine

The preparation was carried out in accordance with general synthesis instructions 4 from 2-methyl-1H-indole and (4-trifluoromethyl-benzylidene)-dimethylammonium chloride, which had been prepared in accordance with example 44 from 4-trifluoromethyl-benzaldehyde and dimethylamine.

Pharmacological Studies

1.) In Vitro Tests

The indole Mannich bases according to the invention were tested for their activity as described above.

The compounds of the general formula 1 according to the invention investigated are suitable as ligands for the α2-subtype of the human α-adrenergic receptor, which is of importance for pain sensation.

The affinity of the compounds according to the invention for this α2-subtype of the α-adrenergic receptor has been determined with the aid of the SPA test such as is described in John P. Devlin, High Throughput Screening, Marcel Dekker Inc. 1997, pages 307 to 316. This literature is introduced herewith as a reference and is therefore part of the disclosure. The affinities of the compounds according to the invention were in each case determined at a concentration of 10 µM.

The results of selected studies are given in the following table 1:

TABLE 1

| Example no. | % Inhibition of α2 (humans), 10 μM |
|---|---|
| 36 | 67 |
| 50 | 51 |
| 34 | 95 |
| 30 | 40 |
| 7 | 68 |
| 15 | 40 |
| 51 | 43 |
| 52 | 37 |
| 53 | 38 |
| 54 | 55 |
| 55 | 49 |
| 56 | 39 |
| 57 | 64 |
| 58 | 82 |
| 59 | 37 |
| 60 | 66 |
| 61 | 63 |
| 62 | 51 |
| 63 | 60 |
| 64 | 48 |
| 65 | 42 |
| 66 | 44 |
| 67 | 36 |
| 68 | 88 |
| 69 | 75 |
| 70 | 63 |
| 71 | 50 |

The compounds according to the invention investigated furthermore also showed an inhibition of serotonin re-uptake.

The results of selected investigations of the inhibition of serotonin re-uptake are reproduced in the following table 2:

TABLE 2

| Example no. | Inhibition of 5HT uptake in % |
|---|---|
| 44 | 48 |
| 72 | 60 |
| 73 | 41 |
| 74 | 72 |
| 75 | 39 |
| 76 | 42 |
| 77 | 38 |
| 78 | 73 |
| 79 | 50 |
| 80 | 42 |
| 81 | 68 |
| 82 | 42 |
| 83 | 39 |
| 84 | 44 |
| 85 | 44 |
| 86 | 41 |
| 87 | 50 |
| 88 | 62 |
| 89 | 45 |
| 90 | 44 |
| 91 | 49 |
| 92 | 46 |
| 93 | 78 |
| 94 | 64 |
| 95 | 70 |
| 96 | 55 |
| 97 | 79 |
| 98 | 66 |
| 99 | 42 |
| 100 | 48 |
| 101 | 41 |
| 102 | 42 |
| 103 | 74 |

2.) Analgesia Test in the Writhing Test in Mice

The in-depth investigation of the compounds according to the invention for their analgesic activity was carried out in the phenylquinone-induced writhing in mice as described above.

The compounds according to the invention investigated showed an analgesic action.

The results of selected writhing investigations are summarized in the following table 3.

TABLE 3

Analgesia test in the writhing test in mice

| Example No. | Inhibition of the writhing reaction in % |
|---|---|
| 22 | 39 |
| 23 | 75 |
| 46 | 41 |
| 47 | 57 |
| 48 | 6 |
| 49 | 82 |

The invention claimed is:

1. A substituted indole compound of formula I

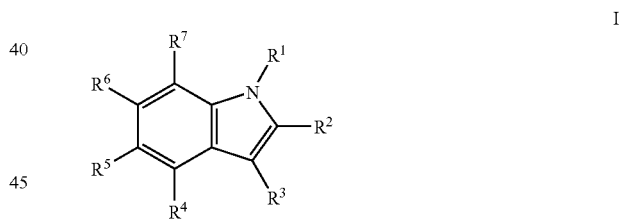

wherein
R$^1$=H, a C$_{1-10}$-alkyl radical, a phenyl or naphthyl radical which is bonded via a C$_{1-6}$-alkylene group, is unsubstituted or at least monosubstituted by an OH, a halogen, a CF$_3$, a CN, a C$_{1-6}$-alkyl, a C$_{1-6}$-alkoxy or a phenyl radical, or a heteroaryl radical which is bonded via a C$_{1-6}$-alkylene group and is unsubstituted or substituted by a halogen, CN, CF$_3$ or OH radical, R$^2$=H, F, Cl, Br, CF$_3$, CN, NO$_2$, NHR$^8$, SR$^9$, OR$^{10}$, SO$_2$NHR$_2$, SO$_2$NHR$^{21}$, CH$_2$CO(OR$^{12}$), COR$^{19}$, a C$_{1-10}$-alkyl radical, a phenyl or naphthyl radical which is unsubstituted or at least monosubstituted by an OH, a halogen, a CF$_3$, a CN, a C$_{1-6}$-alkyl, a C$_{1-6}$-alkoxy or a phenyl radical, a heteroaryl radical which is unsubstituted or substituted by a halogen, CN, CF$_3$ or OH radical, a phenyl or naphthyl radical which is bonded via a C$_{1-6}$-alkylene group, is unsubstituted or at least monosubstituted by an OH, a halogen, a CF$_3$, a CN, a C$_{1-6}$-alkyl, a C$_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^3=CH(R^{13})N(R^{14})(R^{15})$, $R^4$, $R^5$, $R^6$, $R^7$ are identical or different and may be H, F, Cl, Br, $CF_3$, CN, $NO_2$, $NHR^8$, $SR^9$, $OR^{10}$, $SO_2NH_2$, $SO_2NHR^{21}$, $CO(OR^{11})$, $CH_2CO(OR^{12})$, $COR^{19}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a heteroaryl radical which is unsubstituted or substituted by a halogen, CN, $CF_3$ or OH radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a C1–6-alkylene group and is unsubstituted or substituted by a halogen, CN, $CF_3$ or OH radical, $R^8$=H, $COR^{16}$, a $C_{1-10}$-alkyl radical or a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, $R^9$=H, a $C_{1-10}$-alkyl radical or a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, $R^{10}$=H, $COR^{17}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^{11}$=H, a $C_{1-10}$-alkyl radical or a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, $R^{12}$=H, a $C_{1-10}$-alkyl radical or a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, $R^{13}$=an unsubstituted phenyl radical or a phenyl radical which is at least monosubstituted by $C_{1-4}$-alkyl-, halogen-, $CF_3$—, CN— or OH—, $R^{14}$, $R^{15}$ are identical or different and denote a branched or unbranched, saturated or unsaturated, unsubstituted or at least monosubstituted $C_{1-6}$-alkyl radical or an unsubstituted or at least monosubstituted phenyl, benzyl or phenethyl radical, or $R^{14}$ and $R^{15}$ together denote $(CH_2)_n$, where n=an integer from 3 to 6, or $(CH_2)_2O(CH_2)_2$, $R^{16}$=a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is unsubstituted or substituted by a halogen, CN, $CF_3$ or OH radical, $R^{17}$=a $C_{1-10}$-alkyl radical $R^{18}$=a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is unsubstituted or substituted by a halogen, CN, $CF_3$ or OH radical, $R^{19}$=H, $NHNH_2$, $NHR^{20}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a heteroaryl radical which is unsubstituted or substituted by a halogen, CN, $CF_3$ or OH radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^{20}$=H, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a heteroaryl radical which is unsubstituted or substituted by a halogen, CN, $CF_3$ or OH radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^{21}$=H, $COR^{17}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, and/or a racemate, enantiomer, or disastereomer thereof, and/or a corresponding base or a corresponding salt of a physiologically tolerated acid thereof, excluding a compound in which the radical $R^3=CH(R^{13})N(R^{14})(R^{15})$ and a compound wherein the radicals $R^4$ to $R^7$ and $R^2$=H, the radical $R^{13}$=phenyl, the radicals $R^{14}$ and $R^{15}$ together=$(CH_2)_5$ and the radical $R^1$=H, $CH_3$ or benzyl or the radicals $R^4$ to $R^7$ and $R^2$=H, the radical $R^{13}$=phenyl, the radicals $R^{14}$, $R^{15}$ each=$CH_3$ and the radical $R^1$=H, $CH_3$ or benzyl or the radicals $R^4$ to $R^7$ and $R^2$=H, the radical $R^{13}$=phenyl, the radicals $R^{14}$ and $R^{15}$ together=$(CH_2)_4$ and the radical $R^1$=H, $CH_3$, $CH_2$—CH=$CH_2$ or 4-chlorobenzyl and for $R^1$=$CH_3$ also the corresponding hydrochloride of the compound or the radicals $R^4$ to $R^7$, $R^1$ and $R^2$=H, the radical $R^{13}$=phenyl, the radical $R^{14}$=phenyl and the radical $R^{15}$=4-ethoxyphenyl or the radicals $R^4$ to $R^7$ and $R^1$=H, the radical $R^{13}$=phenyl, 2-hydroxyphenyl or 2-hydroxy-5-methylphenyl, the radicals $R^{14}$ and $R^{15}$ together=$(CH_2)_5$ and the radical $R_2$=$CH_3$ and for $R^{13}$=phenyl and the corresponding hydrogen sulfate or the radicals $R^4$ to $R^7$ and $R^1$=H, the radical $R^{13}$=phenyl, the radicals $R^{14}$ and $R^{15}$ together=$(CH_2)_2O(CH_2)_2$ and the radical $R^2$=$CH_3$ and the corresponding hydrogen sulfate of the compound.

2. The substituted indole compound according to claim 1, wherein the radical $R^1$ represents H.

3. The substituted indole compound according to claim 1, wherein the radical $R^1$ represents a $C_{1-6}$-alkyl radical.

4. The substituted indole compound according to claim 1, wherein the radical $R^1$ represents a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

5. The substituted indole compound according to claim 1, wherein the radical $R^2$ represents H.

6. The substituted indole compound according to claim 1, wherein the radical $R^2$ represents a $C_{1-6}$-alkyl radical.

7. The substituted indole compound according to claim 1, wherein the radical $R^2$ represents an unsubstituted phenyl radical.

8. The substituted indole compound according to claim 1, wherein the radical $R^2$ represents a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

9. The substituted indole compound according to claim 1, wherein the radical $R^2$ represents Cl or F.

10. The substituted indole compound according to claim 1, wherein the radical $R^2$ represents $NO_2$.

11. The substituted indole compound according to claim 1, wherein the radical $R^2$ represents $OR^{10}$.

12. The substituted indole compound according to claim 1, wherein at least one of the radicals $R^4$, $R^5$, $R^6$ or $R^7$ represents H.

13. The substituted indole compound according to claim 1, wherein at least one of the radicals $R^4$, $R^5$, $R^6$ or $R^7$ represents Cl or F.

14. The substituted indole compound according to claim 1, wherein at least one of the radicals $R^4$, $R^5$, $R^6$ or $R^7$ represents a $C_{1-6}$-alkyl radical.

15. The substituted indole compound according to claim 1, wherein at least one of the radicals $R^4$, $R^5$, $R^6$ or $R^7$ represents $NO_2$.

16. The substituted indole compound according to claim 1, wherein at least one of the radicals $R^4$, $R^5$, $R^6$ or $R^7$ represents a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

17. The substituted indole compound according to claim 1, wherein at least one of the radicals $R^4$, $R^5$, $R^6$ or $R^7$ represents $OR^{10}$.

18. The substituted indole compound according to claim 1, wherein at least one of the radicals $R^4$, $R^5$, $R^6$ or $R^7$ represents $CO(OR^{11})$.

19. The substituted indole compound according to claim 1, wherein at least one of the radicals $R^4$, $R^5$, $R^6$ or $R^7$ represents a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical.

20. The substituted indole compound according to claim 1, wherein the radical $R^8$ represents a $C_{1-6}$-alkyl radical.

21. The substituted indole compound according to claim 1, wherein the radical $R^9$ represents a $C_{1-6}$-alkyl radical.

22. The substituted indole compound according to claim 1, wherein the radical $R^9$ represents a phenyl radical.

23. The substituted indole compound according to claim 1, wherein the radical $R^{10}$ represents H.

24. The substituted indole compound according to claim 1, wherein the radical $R^{10}$ represents a $C_{1-6}$-alkyl radical.

25. The substituted indole compound according to claim 1, wherein the radical $R^{10}$ represents a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

26. The substituted indole compound according to claim 1, wherein the radical $R^{11}$ represents H.

27. The substituted indole compound according to claim 1, wherein the radical $R^{11}$ represents a $C_{1-6}$-alkyl radical.

28. The substituted indole compound according to claim 1, wherein the radical $R^{12}$ represents a $C_{1-6}$-alkyl radical.

29. The substituted indole compound according to claim 1, wherein the radical $R^{13}$ denotes an unsubstituted phenyl radical or a phenyl radical which is at least monosubstituted by methyl, tert-butyl, F, Cl, Br or $CF_3$.

30. The substituted indole compound according to claim 1, wherein at least one of the radicals $R^{14}$ or $R^{15}$ represents a branched or unbranched, saturated or unsaturated, unsubstituted or at least monosubstituted $C_{1-6}$-alkyl radical.

31. The substituted indole compound according to claim 1, wherein the radicals $R^{14}$ and $R^{15}$ together denote $(CH_2)_n$, where n=4 or 5.

32. The substituted indole compound according to claim 1, wherein the radical $R^{16}$ represents a $C_{1-6}$-alkyl radical.

33. The substituted indole compound according to claim 1, wherein the radical $R^{17}$ represents a $C_{1-6}$-alkyl radical.

34. The substituted indole compound according to claim 1, wherein the radical $R^{18}$ represents a $C_{1-6}$-alkyl radical.

35. The substituted indole compound according to claim 1, wherein the radical $R^{19}$ represents a $C_{1-6}$-alkyl radical.

36. The substituted indole compound according to claim 1, wherein the radical $R^{19}$ represents a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

37. The substituted indole compound according to claim 1, wherein the radical $R^{20}$ represents a $C_{1-6}$-alkyl radical.

38. The substituted indole compound according to claim 1, wherein the radical $R^{20}$ represents a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

39. The substituted indole compound according to claim 1, wherein the radical $R^{21}$ represents H.

40. The substituted indole compound according to claim 1, wherein the radical $R^{21}$ represents a $C_{1-6}$-alkyl radical.

41. The substituted indole compound according to claim 1, wherein the radical $R^{21}$ represents a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

42. The substituted indole compound according to claim 1, wherein said compound is

[(5-fluoro-1H-indol-3-yl)-phenylmethyl]-dimethylamine,

[(1-ethyl-2-phenyl-1H-indol-3-yl)-phenylmethyl]-dimethylamine,

[(5-methoxy-1H-indol-3-yl)-phenylmethyl]-dimethylamine, dimethyl-[(2-methyl-1H-indol-3-yl)-phenylmethyl]-amine, 3-(dimethylaminophenylmethyl)-1H-indol-4-ol, dimethyl-[(4-methyl-1H-indol-3-yl)-phenylmethyl]-amine,

[(5-chloro-1H-indol-3-yl)-phenylmethyl]-dimethylamine,

[(5-benzyloxy-1H-indol-3-yl)-phenylmethyl]-dimethylamine, acetic acid 3-(dimethylaminophenylmethyl)-1H-indol-4-yl ester, {[2-(4-chlorophenyl)-1H-indol-3-yl]-phenylmethyl}-dimethylamine,
dimethyl-[(2-methyl-5-nitro-1H-indol-3-yl)-phenylmethyl]-amine,
dimethyl-[(2-methyl-6-nitro-1H-indol-3-yl)-phenylmethyl]-amine,
[(6-fluoro-2-methyl-1H-indol-3-yl)-phenylmethyl]-dimethylamine,
{[2-(4-fluorophenyl)-1H-indol-3-yl]-phenylmethyl}-dimethylamine,
{[2-(3-chloro-4-fluorophenyl)-1H-indol-3-yl]-phenylmethyl}-dimethylamine,
[(7-ethyl-1H-indol-3-yl)-phenylmethyl]-dimethylamine,
3-(dimethylaminophenylmethyl)-1H-indole-6-carboxylic acid,
1-methyl-3-(morpholin-4-yl-phenylmethyl)-1H-indole,
1-ethyl-2-phenyl-3-(pyrrolidin-1-yl-o-tolylmethyl)-1H-indole,
3-[(2-chlorophenyl)-piperidin-1-yl-methyl]-1-ethyl-2-phenyl-1H-indole,
1-ethyl-2-phenyl-3-(phenylpyrrolidin-1-yl-methyl)-1H-indole,
2-phenyl-3-(pyrrolidin-1-yl-o-tolylmethyl)-1H-indole,
2-phenyl-3-(piperidin-1-yl-o-tolylmethyl)-1H-indole,
3-[(2-chlorophenyl)-piperidin-1-yl-methyl]-2-phenyl-1H-indole,
dimethyl-[(2-phenyl-1H-indole-3-yl)-o-tolyl-methyl]-amine,
2-phenyl-3-(phenylpyrrolidin-1-yl-methyl)-1H-indole,
4-methyl-3-(piperidin-1-yl-o-tolylmethyl)-1H-indole,
5-benzyloxy-3-(phenyl-piperidin-1-yl-methyl)-1H-indole,
[(5-benzyloxy-1H-indol-3-yl)-o-tolylmethyl]-dimethylamine,
{[1-(4-methoxybenzyl)-1H-indol-3-yl]-phenyl-methyl}-dimethylamine,
3-(phenylpyrrolidin-1-yl-methyl)-1H-indole,
5-benzyloxy-3-(phenyl-pyrrolidin-1-yl-methyl)-1H-indole,
[(5-bromo-2-fluoro-phenyl)-(4-nitro-1H-indol-3-yl)-methyl]-dimethyl-amine,
[(5-bromo-2-fluoro-phenyl)-(1-methyl-1H-indol-3-yl)-methyl]-dimethyl-amine,
[(2-chloro-6-fluoro-phenyl)-(2-phenyl-1H-indol-3-yl)methyl]-dimethylamine,
[(2-chloro-6-fluoro-phenyl)-(1-ethyl-2-phenyl-1H-indol-3-yl)-methyl]-dimethylamine,
[(2-chloro-6-fluoro-phenyl)-(4-nitro-1H-indol-3-yl)methyl]-dimethyl -amine,
[(2-chloro-6-fluoro-phenyl)-(1-methyl-1H-indol-3-yl)-methyl]-dimethyl-amine,
[(2-bromo-phenyl)-(4-nitro-1H-indol-3-yl)-methyl]-dimethyl-amine,
[(2-bromo-phenyl)-(1-methyl-1H-indol-3-yl)-methyl]-dimethyl-amine,
[(3-bromo-phenyl)-(7-ethyl-1H-indol-3-yl)-methyl]-dimethyl-amine,
[(3-bromo-phenyl)-(1-methyl-1H-indol-3-yl)-methyl]-dimethyl-amine,
[(4-tert-butyl-phenyl)-(2-methyl-1H-indol-3-yl-)-methyl]-dimethyl-amine,
[(4-tert-butyl-phenyl)-(1-ethyl-2-phenyl-1H-indol-3-yl)-methyl]-dimethyl-amine,
[(4-tert-butyl-phenyl)-(1-methyl-1H-indol-3-yl)-methyl]-dimethyl-amine,
[(2-chloro-4-fluoro-phenyl)-(4-nitro-1H-indol-3-yl)methyl]-dimethyl-amine,
[(2-chloro-4-fluoro-phenyl)-(4-methyl-1H-indol-3-yl)-methyl]-dimethyl-amine,
[(2-chloro-6-fluoro-phenyl)-(2-phenyl-1H-indol-3-yl)-methyl]-dimethyl-amine,
{(2-chloro-6-fluoro-phenyl)-[2-(4-chloro-phenyl)-1H-indol-3-yl]-methyl}-dimethyl-amine,
[(2-chloro-6-fluoro-phenyl)-(1-methyl-1H-indol-3-yl) methyl]-dimethyl-amine,
[(3-chloro-phenyl)-(1-methyl-1H-indol-3-yl)-methyl]-dimethyl-amine,
[(2,3-dichloro-phenyl)-(1-methyl-1H-indol-3-yl)-methyl]-dimethyl-amine,
[(2,4-dichloro-phenyl)-(1-methyl-1H-indol-3-yl)methyl]-dimethyl-amine,
[(4-tert-butyl-phenyl)-(1-ethyl-2-phenyl-1H-indol-3-yl)-methyl]-dimethyl-amine,
[(2-chloro-4-fluoro-phenyl)-(2-methyl-1H-indol-3-yl)-methyl]-dimethyl-amine,
[(2-chloro-6-fluoro-phenyl)-(2-methyl-1H-indol-3-yl)-methyl]-dimethyl-amine,
[(5-chloro-1H-indol-3-yl)-(2-fluoro-phenyl)-methyl]-dimethyl-amine,
[(4-fluoro-phenyl)-(4-methyl-1H-indol-3-yl)-methyl]-dimethyl-amine,
dimethyl-[(2-methyl-1H-indol-3-yl)-o-tolyl-methyl]-amine,
[(7-ethyl-1H-indol-3-yl)-o-tolyl-methyl]-dimethyl-amine,
dimethyl-[(1-methyl-1H-indol-3-yl)-o-tolyl-methyl]-amine,
[(5-chloro-1H-indol-3-yl)-o-tolyl-methyl]-dimethyl-amine,
[(5-chloro-1H-indol-3-yl)-m-tolyl-methyl]-dimethyl-amine,
dimethyl-[(2-methyl-1H-indol-3-yl)-p-tolyl-methyl]-amine,
[(5-chloro-1H-indol-3-yl)-p-tolyl-methyl]-dimethyl-amine,
[(5-chloro-1H-indol-3-yl)-(2-trifluoromethyl-phenyl)-methyl]-dimethyl-amine, or
dimethyl-[(2-methyl-1H-indol-3-yl)-(4-trifluoromethyl-phenyl)-methyl]-amine.

43. A process for the preparation of one or more substituted indole compounds of formula I according to claim 1, said process comprising reacting one or more aromatic aldehyde compounds of formula II

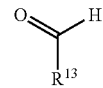

wherein $R^{13}$ has the meaning according to formula I, in solution, in the presence of a base with one or more secondary amines of formula III

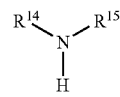

in which the radicals $R^{14}$ and $R^{15}$ have the meaning according to formula I, to give one or more aminal compounds of formula IV

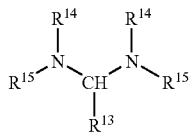

IV reacting said aminal compounds of formula IV without further purification, with an acid chloride in an absolute solvent to give one or more iminium salts of formula V

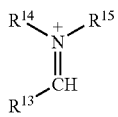

V reacting said iminium salts of formula V without further purification and in solution, with an indole and/or a substituted indole compound of formula VI

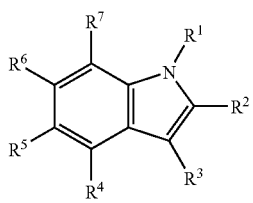

VI in which the radical $R^3$=H and the radicals $R^1$, $R^2$, $R^4$ to $R^{12}$ and $R^{16}$ to $R^{21}$ have the meaning according to formula I, and purifying the substituted indole compounds of formula I by extraction and/or washing, and isolating by conventional methods.

44. A process for the preparation of one or more substituted indole compounds of formula I according to claim 1, in which the radical $R^1$=H and the radicals $R^2$ to $R^{21}$ have the meaning according to formula I, said process comprising reacting one or more aromatic aldehyde compounds of formula II

II wherein $R^{13}$ has the meaning according to formula I, in solution in the presence of a base with one or more secondary amines of formula III

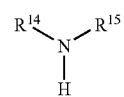

III in which the radicals $R^{14}$ and $R^{15}$ have the meaning according to formula I, to give one or more aminal compounds of formula IV

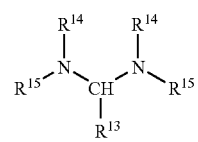

IV reacting said aminal compounds of formula IV without further purification, with an acid chloride in an absolute solvent to give one or more iminium salts of formula V

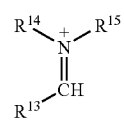

V reacting said iminium salts of formula V without further purification and in solution, with one or more indole and/or substituted indole compounds of formula VI

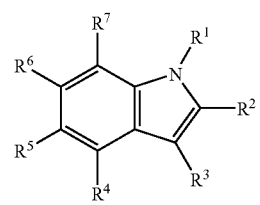

VI in which the radicals $R^1$ and $R^3$ each=H and the radicals $R^2$, $R^4$ $R^{12}$ and $R^{16}$ to $R^{21}$ have the meaning according to formula I, and reacting said compounds of formula VI obtained in this way, in which $R^1$=H and the radicals $R^2$ to $R^{21}$ have the meaning according to formula I, in solution with one or more compounds of formula $XR^{22}$, in which $R^{22}$ denotes a $C_{1-10}$-alkyl radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical and X=Cl, Br or I, in the presence of a base, and the compounds of formula I obtained in this way, in which $R^1$ denotes a $C_{1-10}$-alkyl radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, purifying by filtration, and isolating by conventional methods.

45. The process according to claim 44, wherein the reaction with the compounds of formula $XR^{22}$ is carried out in dimethylsulfoxide.

46. The process according to claim 44, wherein X=Cl.

47. The process according to claim 44, wherein the radical $R^{22}$ represents a $C_{1-6}$-alkyl radical or a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

48. The process according to claim 44, wherein the reaction with the compounds of formula $XR^{22}$ is carried out in the presence of potassium hydroxide.

49. The process according to claim 44, wherein the compounds of formula I are purified by filtration over a scavenger resin.

50. The process according to claim 43, wherein the aromatic aldehyde compounds of formula II are reacted in organic solvents, with one or more secondary amines of formula III.

51. The process according to claim 43, wherein the aromatic aldehyde compounds of formula II are reacted in the presence of potassium carbonate and/or boric acid anhydride as the base.

52. The process according to claim 43, wherein the aminal compounds of formula IV are reacted with acetyl chloride to give one or more iminium salts of formula V.

53. The process according to claim 43, wherein the aminal compounds of formula IV are reacted in absolute diethyl ether to give iminium salts of formula V.

54. A pharmaceutical composition comprising, as the active compound, a therapeutically effective amount of at least one substituted indole compound of formula I

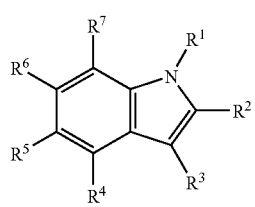

I wherein $R^1$=H, a $C_{1-10}$-alkyl radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, a $C_{1-6}$-alkyl radical or a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical, $R^2$=H, F, Cl, Br, $CF_3$, CN, $NO_2$, $NHR^8$, $SR^9$, $OR^{10}$, $SO_2NH_2$, $SO_2NHR^{21}$, $CH_2CO(OR^{12})$, $COR^{19}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a heteroaryl radical which is unsubstituted or substituted by a halogen, CN, $CF_3$ or OH radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^3$=CH($R^{13}$)N($R^{14}$)($R^{15}$)

$R^4$, $R^5$, $R^6$, $R^7$ are identical or different and=H, F, Cl, Br, $CF_3$, CN, $NO_2$, $NHR^8$, $SR^9$, $OR^{10}$, $SO_2NH_2$, $SO_2NHR^{21}$, $CO(OR^{11})$, $CH_2CO(OR^{12})$, $COR^{19}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a heteroaryl radical which is unsubstituted or substituted by a halogen, CN, $CF_3$ or OH radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^8$=H, $COR^{16}$, a $C_{1-10}$-alkyl radical or a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, $R^9$=H, a $C_{1-10}$-alkyl radical or a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, $R^{10}$=H, $COR^{17}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^{11}$=H, a $C_{1-10}$-alkyl radical or a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, $R^{12}$=H, a $C_{1-10}$-alkyl radical or a phenyl or naplithyl radical which is unsubstituted or at least monosubstituted by an OH, a halogen, a $CF_3$, a CN, a $C_{1-6}$-alkyl, a $C_{1-6}$-alkoxy or a phenyl radical, $R^{13}$=a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a heteroaryl radical which is unsubstituted or substituted by a halogen, CN, $CF_3$ or OH radical, or an alkyl radical without an acid proton in the α-position, $R^{14}$, $R^{15}$ are identical or different and denote a branched or unbranched, saturated or unsaturated, unsubstituted or at least monosubstituted $C_{1-6}$-alkyl radical or an unsubstituted or at least monosubstituted phenyl, benzyl or phenethyl radical, or $R^{14}$ and $R^{15}$ together denote $(CH_2)_n$, where n=an integer from 3 to 6, or $(CH_2)_2O(CH_2)_2$, $R^{16}$=a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is unsubstituted or substituted by a halogen, CN, $CF_3$ or OH radical, $R^{17}$=a $C_{1-10}$-alkyl radical, $R^{18}$=a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is unsubstituted or substituted by a halogen, CN, $CF_3$ or OH radical, $R^{19}$=H, $NHNH_2$, $NHR^{20}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a heteroaryl radical which is unsubstituted or substituted by a halogen, CN, $CF_3$ or OH radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^{20}$=H, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a heteroaryl radical which is unsubstituted or substituted by a halogen, CN, $CF_3$ or OH radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, $R^{21}$=H, $COR^{17}$, a $C_{1-10}$-alkyl radical, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a phenyl or naphthyl radical which is bonded via a $C_{1-6}$-alkylene group, is unsubstituted or at least monosubstituted by an OH, a halogen, a $CF_3$, a CN, a $C_{1-6}$-alkyl, a $C_{1-6}$-alkoxy or a phenyl radical, or a heteroaryl radical which is bonded via a $C_{1-6}$-alkylene group and is unsubstituted or substituted by a halogen, CN, $CF_3$ or OH radical, and/or a racemate, enantiomer, or diastereomer thereof, and/or a corresponding base or a corresponding salt of a physiologically tolerated acid thereof; and a pharmaceutically-acceptable auxilliary substance.

55. The substituted indole compound according to claim 3, wherein $R^1$ is a $C_{1-2}$-alkyl radical.

56. The substituted indole compound according to claim 6, wherein $R^2$ is a $C_{1-2}$-alkyl radical.

57. The substituted indole compound according to claim 14, wherein at least one of the radicals $R^4$, $R^5$, $R^6$ or $R^7$ is a $C_{1-2}$-alkyl radical.

58. The substituted indole compound according to claim 19, wherein at least one of the radicals $R^4$, $R^5$, $R^6$ or $R^7$ is an unsubstituted phenyl radical.

59. The substituted indole compound according to claim 29, wherein the radical $R^{13}$ is 2-methyl-phenyl, 3-methyl-phenyl, 4-methyl-phenyl, 2-tert-butyl-phenyl, 3-tert-butyl-phenyl, 4-tert-butyl-phenyl, 2-fluorophenyl, 3-fluoro-phenyl, 4-fluoro-phenyl, 2-chlorophenyl, 3-chloro-phenyl, 4-chloro-phenyl, 2-bromophenyl, 3-bromo-phenyl, 4-bromo-phenyl, 5-bromo-2-fluoro-phenyl, 2-chloro-4-fluoro-phenyl, 2-chloro-5-fluoro-phenyl, 2-chloro-6-fluoro-phenyl, 4-bromo-2-fluoro-phenyl, 3-bromo-4-fluoro-phenyl, 3-bromo-2-fluoro-phenyl, 2,3-dichloro-phenyl, 2,4-dichlorophenyl, 2,5-dichlorophenyl, 3,4-dichloro-phenyl, 2,3-dimethyl-phenyl, 2,4-dimethyl-phenyl, 2,5-dimethylphenyl, 2-trifluoromethyl-phenyl, 3-trifluoromethyl-phenyl or 4-trifluoromethyl-phenyl.

60. The substituted indole compound according to claim 29, wherein $R^{13}$ is an unsubstituted phenyl radical.

61. The substituted indole compound according to claim 30, wherein at least one of the radicals $R^{14}$ or $R^{15}$ is a $CH_3$ radical.

62. The process of claim 43, wherein $R^{13}$ is reacted with the one or more secondary amines at a temperature of from −10 to 110° C.

63. The process of claim 43, wherein the iminium salts of formula V are reacted in a solution comprising acetonitrile, toluene or mixtures thereof.

64. The process of claim 43, wherein the substituted indole compounds of formula I are purified by washing with acetone.

65. The process of claim 44, wherein the aromatic aldehyde compounds of formula II are reacted with one or more secondary amines of formula III at a temperature of from −10 to 110° C.

66. The process of claim 44, wherein the iminium salts of formula V are reacted with one or more indole compounds of formula VI in a solution comprising acetonitrile, toluene or mixtures thereof.

67. The process of claim 44, wherein compounds of formula VI are reacted with compounds of formula $XR^{22}$ at a temperature of from 10 to 150° C.

68. The process of claim 49, wherein the scavenger resin is polymer-bonded tris(2-aminoethyl)-amine, 3-(3-mercaptophenyl)propane-amidomethylpolystyrene or mixtures thereof.

69. The process of claim 50, wherein the organic solvent is toluene.

70. The process according to claim 44, wherein the aromatic aldehyde compounds of formula II are reacted in organic solvents, with one or more secondary amines of formula III.

71. The process of claim 70, wherein the organic solvent is toluene.

72. The process of claim 44, wherein the aromatic aldehyde compounds of formula II are reacted in the presence of potassium carbonate and/or boric acid anhydride as the base.

73. The process of claim 44, wherein the aminal compounds of formula IV are reacted with acetyl chloride to give one or more iminium salts of formula V.

74. The process of claim 44, wherein the aminal compounds of formula IV are reacted in absolute diethyl ether to give iminium salts of formula V.

75. The pharmaceutical composition of claim 54, wherein $R^1$ is H.

76. The pharmaceutical composition of claim 54, wherein $R^1$ is H or a $C_{1-2}$-alkyl radical.

77. The pharmaceutical composition of claim 54, wherein $R^2$ is H, Cl, F, $NO_2$, $OR^{10}$, a $C_{1-6}$-alkyl radical or a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

78. The pharmaceutical composition of claim 54, wherein $R^2$ is H, a $C_{1-2}$-alkyl, or an unsubstituted phenyl radical.

79. The pharmaceutical composition of claim 54, wherein $R^4$, $R^5$, $R^6$, or $R^7$ is H, Cl, F, $NO_2$, $OR^{10}$, $CO(OR^{11})$, a phenyl or naphthyl radical which is unsubstituted or at least monosubstituted by an OH, a halogen, a $CF_3$, a CN, a $C_{1-6}$-alkyl, a $C_{1-6}$-alkoxy or a phenyl radical, a $C_{1-6}$-alkyl radical or a phenyl or naphthyl radical which is bonded via a $C_{1-2}$-alkylene group with further rings.

80. The pharmaceutical composition of claim 54, wherein $R^4$, $R^5$, $R^6$ or $R^7$ is H, $NO_2$, a $C_{1-2}$-alkyl, or an unsubstituted phenyl radical.

81. The pharmaceutical composition of claim 54, wherein $R^8$ is a $C_{1-6}$-alkyl radical.

82. The pharmaceutical composition of claim 54, wherein $R^9$ is a $C_{1-6}$-alkyl or a phenyl radical.

83. The pharmaceutical composition of claim 54, wherein $R^{10}$ is H, a $C_{1-6}$-alkyl radical or a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

84. The pharmaceutical composition of claim 54, wherein $R^{11}$ is H or a $C_{1-6}$-alkyl radical.

85. The pharmaceutical composition of claim 54, wherein $R^{12}$ is a $C_{1-6}$-alkyl radical.

86. The pharmaceutical composition of claim 54, wherein $R^{13}$ is an unsubstituted phenyl radical or a phenyl, thiophene or furfuryl radical which is at least monosubstituted by $C_{1-4}$-alkyl-, $C_{1-3}$-alkoxy-, halogen-, $CF_3$—, CN—, O-phenyl- or OH.

87. The pharmaceutical composition of claim 54, wherein $R^{13}$ is 2-methoxy-phenyl, 3-methoxy phenyl, 4-methoxy-phenyl, 2-methyl-phenyl, 3-methyl-phenyl, 4-methyl-phenyl, 2-tert-butyl-phenyl, 3-tert-butyl-phenyl, 4-tert-butyl-phenyl, 2-fluoro-phenyl, 3-fluoro-phenyl, 4-fluoro-phenyl, 2-chloro-phenyl, 3-chloro-phenyl, 4-chloro-phenyl, 2-bromo-phenyl, 3-bromo-phenyl, 4-bromo-phenyl, 5-bromo-2-fluoro-phenyl, 2-chloro-4-fluoro-phenyl, 2-chloro-5-fluoro-phenyl, 2-chloro-6-fluoro-phenyl, 4-bromo-2-fluoro-phenyl, 3-bromo-4-fluoro-phenyl, 3-bromo-2-fluoro-phenyl, 2,3-dichloro-phenyl, 2,4-dichloro-phenyl, 2,5-dichlorophenyl, 3,4-dichloro-phenyl, 2,3-dimethyl-phenyl, 2,4-dimethyl-phenyl, 2,5-dimethylphenyl, 2,3-dimethoxy-phenyl, 2,4-dimethoxy-phenyl, 2,5-dimethoxy-phenyl, 3,4-dimethoxy-phenyl, 3,4,5-trimethoxy-phenyl, 2-trifluoromethyl-phenyl, 3-trifluoromethyl-phenyl or 4-trifluoromethyl-phenyl radical.

88. The pharmaceutical composition of claim 54, wherein $R^{13}$ is an unsubstituted phenyl, thiophene or furfuryl radical.

89. The pharmaceutical composition of claim 54, wherein $R^{14}$ or $R^{15}$ is a saturated, unsubstituted or at least monosubstituted $C_{1-6}$-alkyl radical.

90. The pharmaceutical composition of claim 54, wherein $R^{14}$ or $R^{15}$ is a $CH_3$ radical.

91. The pharmaceutical composition of claim 54, wherein $R^{14}$ and $R^{15}$ together denote $(CH_2)_n$ where n=4 or 5.

92. The pharmaceutical composition of claim 54, wherein $R^{16}$ is a $C_{1-6}$-alkyl radical.

93. The pharmaceutical composition of claim 54, wherein $R^{17}$ is a $C_{1-6}$-alkyl radical.

94. The pharmaceutical composition of claim 54, wherein $R^{18}$ a $C_{1-6}$-alkyl radical.

95. The pharmaceutical composition of claim 54, wherein $R^{19}$ is a $C_{1-6}$-alkyl radical or a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

96. The pharmaceutical composition of claim 54, wherein $R^{20}$ is a $C_{1-6}$-alkyl radical or a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

97. The pharmaceutical composition of claim 54, wherein $R^{21}$=H, a $C_{1-6}$-alkyl radical or a phenyl or naphthyl radical which is bonded via a $C_{1-2}$-alkylene group, is unsubstituted or at least monosubstituted by an OH, a halogen, a $CF_3$, a CN, a $C_{1-6}$-alkyl, a $C_{1-6}$-alkoxy or a phenyl radical.

98. A process of providing analgesic action, comprising administering to a patient in need thereof a therapeutically effective amount of the substituted indole compound according to claim 1.

* * * * *